(12) United States Patent
Aebi et al.

(10) Patent No.: US 10,035,804 B2
(45) Date of Patent: *Jul. 31, 2018

(54) SPIRODIAMINE DERIVATIVES AS ALDOSTERONE SYNTHASE INHIBITORS

(71) Applicant: Hoffmann-La Roche Inc., Little Falls, NJ (US)

(72) Inventors: Johannes Aebi, Binningen (CH); Kurt E. Amrein, Itingen (CH); Junli Chen, Shanghai (CN); Benoit Hornsperger, Altkirch (FR); Bernd Kuhn, Reinach BL (CH); Yongfu Liu, Shanghai (CN); Dongbo Li, Shanghai (CN); Hans Peter Maerki, Basel (CH); Rainer E. Martin, Basel (CH); Alexander Mayweg, Basel (CH); Xuefei Tan, Shanghai (CN); Jun Wu, Shanghai (CN); Jianhua Yu, Shanghai (CN)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/479,701

(22) Filed: Apr. 5, 2017

(65) Prior Publication Data

US 2017/0204107 A1    Jul. 20, 2017

Related U.S. Application Data

(63) Continuation of application No. PCT/EP2015/072887, filed on Oct. 5, 2015.

(30) Foreign Application Priority Data

Oct. 8, 2014 (CN) .................. PCT/CN2014/088133

(51) Int. Cl.
  *C07D 487/10* (2006.01)
  *C07D 471/10* (2006.01)
(52) U.S. Cl.
  CPC ......... *C07D 487/10* (2013.01); *C07D 471/10* (2013.01)

(58) Field of Classification Search
  CPC .......................... C07D 401/14; C07D 413/14
  See application file for complete search history.

(56) References Cited

U.S. PATENT DOCUMENTS

| 9,505,742 | B2 * | 11/2016 | Aebi | .................... | C07D 401/14 |
| 9,695,151 | B2 * | 7/2017 | Aebi | .................... | C07D 401/14 |
| 9,695,152 | B2 * | 7/2017 | Aebi | .................... | C07D 401/14 |
| 2013/0143863 | A1 | 6/2013 | Aebi et al. | | |

FOREIGN PATENT DOCUMENTS

WO    2013/033059 A1    3/2013

OTHER PUBLICATIONS

ISR for PCT/EP2015/072887 (dated Dec. 8, 2015).
Written Opinion for ISR for PCT/EP2015/072887.

* cited by examiner

*Primary Examiner* — Alexander R Pagano
*Assistant Examiner* — Ebenezer O Sackey
(74) *Attorney, Agent, or Firm* — Brian L. Buckwalter

(57) ABSTRACT

The invention provides novel compounds having the general formula (I)

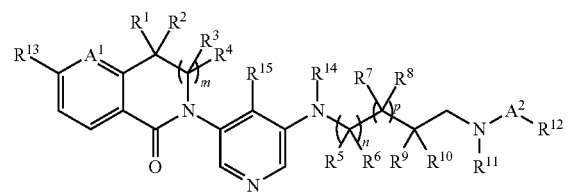

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^5$, $A^1$, $A^2$, m, n and p are as described herein, compositions including the compounds and methods of using the compounds.

20 Claims, No Drawings

SPIRODIAMINE DERIVATIVES AS ALDOSTERONE SYNTHASE INHIBITORS

CROSS REFERENCE TO RELATED APPLICATIONS

This application is a continuation of International Application No. PCT/EP2015/072887 having an international filing date of Oct. 5, 2015 and which claims benefit under 35 U.S.C. § 119 to International Application PCT/CN2014/088133 filed Oct. 8, 2014. The entire contents of both are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

Inhibitors of aldosterone synthase can potentially protect organs and/or tissues from damage caused by an absolute or relative excess of aldosterone. Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will also reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

BRIEF SUMMARY OF THE INVENTION

The present invention provides novel compounds of formula (I)

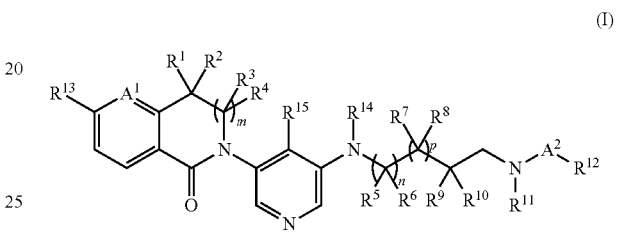

(I)

wherein
$R^1$, $R^2$, $R^3$ and $R^4$ are independently selected from H, alkyl and cycloalkyl;
or $R^1$ and $R^2$ together form —$CH_2$—$CH_2$—;
$R^5$ and $R^6$ are independently selected from H or alkyl;
$A^1$ is —CH— or —N—;
$A^2$ is —C(O)— or —S(O)$_2$—;
$R^{12}$ is heteroaryl or substituted heteroaryl, wherein substituted heteroaryl is substituted with one to three substituent independently selected from alkyl, cycloalkyl, haloalkyl, hydroxy, alkoxy, cyano and halogen;
$R^{13}$ is halogen, cyano, alkoxy or haloalkoxy;
$R^{15}$ is H, alkyl, cycloalkyl or halogen;
m is zero or 1; and
$R^9$ and $R^{14}$ together form —$CH_2$—, $R^{10}$ and $R^{11}$ together form —$CH_2$—, n is 1 and p is zero; or
$R^9$ and $R^{14}$ together form —$CH_2$—$CH_2$—, $R^{10}$ and $R^{11}$ together form —$CH_2$—, n is 1 and p is 1 and $R^7$ and $R^8$ are independently selected from H or alkyl; or
$R^7$ and $R^{14}$ together form —$CH_2$—, $R^8$ and $R^{11}$ together form —$CH_2$—$CH_2$—, n is 1, p is 1 and $R^9$ and $R^{10}$ are independently selected from H or alkyl;
or a pharmaceutically acceptable salt thereof.

In another embodiment, the present inventions provide for pharmaceutical compositions comprising compounds of Formula I.

In another embodiment, the present invention provides aldosterone synthase inhibitors for therapy in a mammal useful for the treatment or prophylaxis of chronic kidney disease, congestive heart failure, hypertension, primary aldosteronism and Cushing syndrome.

DETAILED DESCRIPTION OF THE INVENTION

There is ample preclinical evidence that MR (Mineralcorticoid Receptor)-antagonists (spironolactone and eplerenone) improve blood pressure, cardiac and renal function in various pre-clinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LC1699, to patients with primary aldosteronism, lead to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate different CYP11B2 inhibitors.

The compounds of the present invention according formula (I) are potent inhibitors of CYPB11B2 and present an improved selectivity towards CYP11B2 versus CYP11B1 combined with an improved metabolic stability.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of chronic kidney disease, congestive heart failure, hypertension, primary aldosteronism and Cushing syndrome and the use of the said compounds, salts or esters for the production of medicaments for the treatment or prophylaxis of chronic kidney disease, congestive heart failure, hypertension, primary aldosteronism and Cushing syndrome.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl and isopropyl, n-butyl, iso-butyl, sec-butyl, and. Particular alkyl groups include methyl, ethyl and isopropyl.

The term "aryl" denotes a monovalent aromatic carbocyclic mono- or bicyclic ring system comprising 6 to 10 carbon ring atoms. Examples of aryl moieties include phenyl and naphthyl. Particular aryl group is phenyl.

The term "cyano" denotes a —C≡N group.

The term "cycloalkyl" denotes a monovalent saturated monocyclic hydrocarbon group of 3 to 10 ring carbon atoms. In particular embodiments, cycloalkyl denotes a monovalent saturated monocyclic hydrocarbon group of 3 to 8 ring carbon atoms. Examples for cycloalkyl are cyclopropyl, cyclobutanyl, cyclopentyl, cyclohexyl or cycloheptyl. Particular cycloalkyl group is cyclopropyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy.

The term "halogen" and "halo" are used interchangeably herein and denote fluoro, chloro, bromo, or iodo. Particular halogens are chloro and fluoro. Particular halogen is fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl are imidazolyl, oxazolyl, pyridinyl, pyrazinyl, pyrazolyl, pyridazinyl, pyrimidinyl, isoxazolyl. Particular heteroaryl is and pyrazolyl.

The term "hydroxy" denotes an —OH group.

The term "pharmaceutically acceptable salt(s)" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. μ Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol M.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H ("T"), $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically labeled compounds of the present invention (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting a non-isotopically labeled reagent with a isotopically labeled reagent. In particular, compounds of formula (I) wherein one or more H atom have been replaced by a $^2$H atom are also an embodiment of this invention.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Also an embodiment of the present invention are compounds according to formula (I) as described herein wherein $R^1$ and $R^2$ are alkyl or $R^1$ and $R^2$ together form —CH$_2$—CH$_2$—.

A particular embodiment of the present invention are compounds according to formula (I) as described herein, wherein $R^1$ and $R^2$ are alkyl.

Another embodiment of the present invention are compounds according to formula (I) as described herein, wherein $R^3$ and $R^4$ are H.

Also an embodiment of the present invention are compounds according to formula (I) as described herein, wherein $R^{13}$ is Halogen.

A further embodiment of the present invention are compounds according to formula (I) as described herein, wherein $R^{15}$ is H.

Another particular embodiment of the present invention are compounds according to formula (I) as described herein, wherein $A^1$ is —CH—.

Also a particular embodiment of the present invention are compounds according to formula (I) as described herein, wherein $A^2$ is —C(O)—.

Another embodiment of the present invention are compounds according to formula (I) as described herein, wherein $R^9$ and $R^{14}$ together form —CH$_2$—, $R^{10}$ and $R^{11}$ together form —CH$_2$—, n is 1 and p is zero.

Another particular embodiment of the present invention are compounds according to formula (I) as described herein, wherein the heteroaryl group from $R^{12}$ are selected from imidazolyl, isoxazolyl, oxazolyl, pyrazinyl, pyrazolyl, pyridazinyl, pyridinyl and pyrimidinyl.

Another embodiment of the present invention are compounds according to formula (I) as described herein, wherein $R^{12}$ is pyrazolyl substituted by alkyl or pyridinyl substituted by alkyl.

A particular embodiment of the present invention are compounds according to formula (I) as described herein, wherein $R^{12}$ is pyrazolyl substituted by alkyl.

Particular examples of compounds of formula (I) as described herein are selected from 5-Chloro-3,3-dimethyl-2-[5-[2-(1-methylpyrazole-4-carbonyl)-2,6-diazaspiro[3.3]heptan-6-yl]-3-pyridyl]isoindolin-1-one;

5-Chloro-2-[5-[2-(1-ethylpyrazole-4-carbonyl)-2,6-diazaspiro[3.3]heptan-6-yl]-3-pyridyl]-3,3-dimethyl-isoindolin-1-one;

5-Chloro-2-[5-[2-(1-isopropylpyrazole-4-carbonyl)-2,6-diazaspiro[3.3]heptan-6-yl]-3-pyridyl]-3,3-dimethyl-isoindolin-1-one;

5-Chloro-3,3-dimethyl-2-[5-[2-(1-methylimidazole-2-carbonyl)-2,6-diazaspiro[3.3]heptan-6-yl]-3-pyridyl]isoindolin-1-one;

5-Chloro-3,3-dimethyl-2-[5-[2-(2-methylpyrazole-3-carbonyl)-2,6-diazaspiro[3.3]heptan-6-yl]-3-pyridyl]isoindolin-1-one;

5-Chloro-3,3-dimethyl-2-[5-[2-(3-methylimidazole-4-carbonyl)-2,6-diazaspiro[3.3]heptan-6-yl]-3-pyridyl]isoindolin-1-one;

5-Chloro-3,3-dimethyl-2-[5-[2-(4-methylpyridine-3-carbonyl)-2,6-diazaspiro[3.3]heptan-6-yl]-3-pyridyl]isoindolin-1-one;

3,3-Dimethyl-2-[5-[2-(1-methylpyrazole-4-carbonyl)-2,6-diazaspiro[3.3]heptan-6-yl]-3-pyridyl]-1-oxo-isoindoline-5-carbonitrile;

2-[5-[2-(1-Ethylpyrazole-4-carbonyl)-2,6-diazaspiro[3.3]heptan-6-yl]-3-pyridyl]-3,3-dimethyl-1-oxo-isoindoline-5-carbonitrile;

2-[5-[2-(1-Isopropylpyrazole-4-carbonyl)-2,6-diazaspiro[3.3]heptan-6-yl]-3-pyridyl]-3,3-dimethyl-1-oxo-isoindoline-5-carbonitrile;

3,3-Dimethyl-2-[5-[2-(1-methylimidazole-2-carbonyl)-2,6-diazaspiro[3.3]heptan-6-yl]-3-pyridyl]-1-oxo-isoindoline-5-carbonitrile;

3,3-Dimethyl-2-[5-[2-(2-methylpyrazole-3-carbonyl)-2,6-diazaspiro[3.3]heptan-6-yl]-3-pyridyl]-1-oxo-isoindoline-5-carbonitrile;

3,3-Dimethyl-2-[5-[2-(3-methylimidazole-4-carbonyl)-2,6-diazaspiro[3.3]heptan-6-yl]-3-pyridyl]-1-oxo-isoindoline-5-carbonitrile;

3,3-Dimethyl-2-[5-[2-(4-methylpyridine-3-carbonyl)-2,6-diazaspiro[3.3]heptan-6-yl]-3-pyridyl]-1-oxo-isoindoline-5-carbonitrile;

2-Methoxy-7,7-dimethyl-6-[5-[2-(1-methylpyrazole-4-carbonyl)-2,6-diazaspiro[3.3]heptan-6-yl]-3-pyridyl]pyrrolo[3,4-b]pyridin-5-one;

2-Methoxy-7,7-dimethyl-6-[5-[2-(4-methylpyridine-3-carbonyl)-2,6-diazaspiro[3.3]heptan-6-yl]-3-pyridyl]pyrrolo[3,4-b]pyridin-5-one;

2-Methoxy-7,7-dimethyl-6-[5-[2-(2-methylpyrazole-3-carbonyl)-2,6-diazaspiro[3.3]heptan-6-yl]-3-pyridyl]pyrrolo[3,4-b]pyridin-5-one;

5-Chloro-3-methyl-2-[5-[2-(1-methylpyrazole-4-carbonyl)-2,6-diazaspiro[3.3]heptan-6-yl]-3-pyridyl]isoindolin-1-one;

5'-Chloro-2'-[5-[2-(1-methylpyrazole-4-carbonyl)-2,6-diazaspiro[3.3]heptan-6-yl]-3-pyridyl]spiro[cyclopropane-1,3'-isoindoline]-1'-one;

5'-Chloro-2'-[5-[2-(4-methylpyridine-3-carbonyl)-2,6-diazaspiro[3.3]heptan-6-yl]-3-pyridyl]spiro[cyclopropane-1,3'-isoindoline]-1'-one;

5'-Chloro-2'-[5-[2-(2-methylpyrazole-3-carbonyl)-2,6-diazaspiro[3.3]heptan-6-yl]-3-pyridyl]spiro[cyclopropane-1,3'-isoindoline]-1'-one;

(3R or 3S)-5-Chloro-3-methyl-2-[5-[2-(1-methylpyrazole-4-carbonyl)-2,6-diazaspiro[3.3]heptan-6-yl]-3-pyridyl]isoindolin-1-one;

(3S or 3R)-5-Chloro-3-methyl-2-[5-[2-(1-methylpyrazole-4-carbonyl)-2,6-diazaspiro[3.3]heptan-6-yl]-3-pyridyl]isoindolin-1-one;

5-Chloro-2-[5-[2-(4-methoxypyridine-3-carbonyl)-2,6-diazaspiro[3.3]heptan-6-yl]-3-pyridyl]-3,3-dimethyl-isoindolin-1-one;

5-Chloro-2-[5-[2-(3,6-dimethylpyrazine-2-carbonyl)-2,6-diazaspiro[3.3]heptan-6-yl]-3-pyridyl]-3,3-dimethyl-isoindolin-1-one;

5-Chloro-2-[5-[2-(1,5-dimethylpyrazole-4-carbonyl)-2,6-diazaspiro[3.3]heptan-6-yl]-3-pyridyl]-3,3-dimethyl-isoindolin-1-one;

5-Chloro-3,3-dimethyl-2-[5-[2-(3-methylisoxazole-4-carbonyl)-2,6-diazaspiro[3.3]heptan-6-yl]-3-pyridyl]isoindolin-1-one;

5-Chloro-3,3-dimethyl-2-[5-[2-(6-methylpyrazine-2-carbonyl)-2,6-diazaspiro[3.3]heptan-6-yl]-3-pyridyl]isoindolin-1-one;

5-Chloro-3,3-dimethyl-2-[5-[2-(4-methylpyrimidine-5-carbonyl)-2,6-diazaspiro[3.3]heptan-6-yl]-3-pyridyl]isoindolin-1-one;

5-Chloro-3,3-dimethyl-2-[5-[2-(5-methylpyrazine-2-carbonyl)-2,6-diazaspiro[3.3]heptan-6-yl]-3-pyridyl]isoindolin-1-one;

5-Chloro-2-[5-[2-(2,5-dimethylpyrazole-3-carbonyl)-2,6-diazaspiro[3.3]heptan-6-yl]-3-pyridyl]-3,3-dimethyl-isoindolin-1-one;

5-Chloro-3,3-dimethyl-2-[5-[2-(5-methyloxazole-4-carbonyl)-2,6-diazaspiro[3.3]heptan-6-yl]-3-pyridyl]isoindolin-1-one;

5-Chloro-3,3-dimethyl-2-[5-[2-(pyrimidine-2-carbonyl)-2,6-diazaspiro[3.3]heptan-6-yl]-3-pyridyl]isoindolin-1-one;

5-Chloro-3,3-dimethyl-2-[5-[2-(5-methylpyrimidine-2-carbonyl)-2,6-diazaspiro[3.3]heptan-6-yl]-3-pyridyl]isoindolin-1-one;

5-Chloro-2-[5-[2-[3-(difluoromethyl)-1-methyl-pyrazole-4-carbonyl]-2,6-diazaspiro[3.3]heptan-6-yl]-3-pyridyl]-3,3-dimethyl-isoindolin-1-one;

5-[6-[5-(6-Chloro-1,1-dimethyl-3-oxo-isoindolin-2-yl)-3-pyridyl]-2,6-diazaspiro[3.3]heptane-2-carbonyl]pyridine-3-carbonitrile;

5-Chloro-2-[5-[2-(3-methoxypyrazine-2-carbonyl)-2,6-diazaspiro[3.3]heptan-6-yl]-3-pyridyl]-3,3-dimethyl-isoindolin-1-one;

5-Chloro-3,3-dimethyl-2-[5-[2-(pyrazine-2-carbonyl)-2,6-diazaspiro[3.3]heptan-6-yl]-3-pyridyl]isoindolin-1-one;

5-Chloro-3,3-dimethyl-2-[5-[2-(5-methylisoxazole-4-carbonyl)-2,6-diazaspiro[3.3]heptan-6-yl]-3-pyridyl]isoindolin-1-one;

5-Chloro-3,3-dimethyl-2-[5-[2-(pyrimidine-5-carbonyl)-2,6-diazaspiro[3.3]heptan-6-yl]-3-pyridyl]isoindolin-1-one;

5-Chloro-3,3-dimethyl-2-[5-[2-(4-methyloxazole-5-carbonyl)-2,6-diazaspiro[3.3]heptan-6-yl]-3-pyridyl]isoindolin-1-one;

5-Chloro-3,3-dimethyl-2-[5-[2-(oxazole-4-carbonyl)-2,6-diazaspiro[3.3]heptan-6-yl]-3-pyridyl]isoindolin-1-one;

5-Chloro-3,3-dimethyl-2-[5-[2-(2-methyloxazole-5-carbonyl)-2,6-diazaspiro[3.3]heptan-6-yl]-3-pyridyl]isoindolin-1-one;

5-Chloro-2-[5-[2-(2,4-dimethyloxazole-5-carbonyl)-2,6-diazaspiro[3.3]heptan-6-yl]-3-pyridyl]-3,3-dimethyl-isoindolin-1-one;

5-Chloro-3,3-dimethyl-2-[5-[2-(2-methyloxazole-4-carbonyl)-2,6-diazaspiro[3.3]heptan-6-yl]-3-pyridyl]isoindolin-1-one;

2-[6-[5-(6-Chloro-1,1-dimethyl-3-oxo-isoindolin-2-yl)-3-pyridyl]-2,6-diazaspiro[3.3]heptane-2-carbonyl]pyridine-3-carbonitrile;

5-Chloro-2-[5-[2-(5-chloro-2-methyl-pyrimidine-4-carbonyl)-2,6-diazaspiro[3.3]heptan-6-yl]-3-pyridyl]-3,3-dimethyl-isoindolin-1-one;

5-Chloro-2-[5-[2-(4,6-dimethylpyrimidine-5-carbonyl)-2,6-diazaspiro[3.3]heptan-6-yl]-3-pyridyl]-3,3-dimethyl-isoindolin-1-one;

5-Chloro-2-[5-[2-(2,4-dimethylpyridine-3-carbonyl)-2,6-diazaspiro[3.3]heptan-6-yl]-3-pyridyl]-3,3-dimethyl-isoindolin-1-one;

3-[6-[5-(6-Chloro-1,1-dimethyl-3-oxo-isoindolin-2-yl)-3-pyridyl]-2,6-diazaspiro[3.3]heptane-2-carbonyl]pyridine-4-carbonitrile;

(3S or 3R)-5-Chloro-2-[5-[2-(1-ethylpyrazole-4-carbonyl)-2,6-diazaspiro[3.3]heptan-6-yl]-3-pyridyl]-3-methyl-isoindolin-1-one;

(3R or 3S)-5-Chloro-2-[5-[2-(1-ethylpyrazole-4-carbonyl)-2,6-diazaspiro[3.3]heptan-6-yl]-3-pyridyl]-3-methyl-isoindolin-1-one;

6-Chloro-2-[5-[2-(1-methylpyrazole-4-carbonyl)-2,6-diazaspiro[3.3]heptan-6-yl]-3-pyridyl]-3,4-dihydroisoquinolin-1-one;

(3R or 3S)-5-Chloro-3-methyl-2-[4-methyl-5-[2-(1-methylpyrazole-4-carbonyl)-2,6-diazaspiro[3.3]heptan-6-yl]-3-pyridyl]isoindolin-1-one;

(3S or 3R)-5-Chloro-3-methyl-2-[4-methyl-5-[2-(1-methylpyrazole-4-carbonyl)-2,6-diazaspiro[3.3]heptan-6-yl]-3-pyridyl]isoindolin-1-one;

5-Chloro-3,3-dimethyl-2-[5-[7-(1-methylpyrazole-4-carbonyl)-2,7-diazaspiro[3.5]nonan-2-yl]-3-pyridyl]isoindolin-1-one;

5-Chloro-3,3-dimethyl-2-[5-[7-(4-methylpyridine-3-carbonyl)-2,7-diazaspiro[3.5]nonan-2-yl]-3-pyridyl]isoindolin-1-one;

5-Chloro-2-[5-[7-(1-ethylpyrazole-4-carbonyl)-2,7-diazaspiro[3.5]nonan-2-yl]-3-pyridyl]-3,3-dimethyl-isoindolin-1-one;

5-Chloro-3,3-dimethyl-2-[5-[2-(1-methylpyrazole-4-carbonyl)-2,7-diazaspiro[3.5]nonan-7-yl]-3-pyridyl]isoindolin-1-one;

5-Chloro-2-[5-[2-(1-ethylpyrazole-4-carbonyl)-2,7-diazaspiro[3.5]nonan-7-yl]-3-pyridyl]-3,3-dimethyl-isoindolin-1-one;

5-Chloro-3,3-dimethyl-2-[5-[2-(4-methylpyridine-3-carbonyl)-2,7-diazaspiro[3.5]nonan-7-yl]-3-pyridyl]isoindolin-1-one; and and pharmaceutically acceptable salts thereof.

Further particular examples of compounds of formula (I) as described herein are selected from 5-Chloro-3,3-dimethyl-2-[5-[2-(1-methylpyrazole-4-carbonyl)-2,6-diazaspiro[3.3]heptan-6-yl]-3-pyridyl]isoindolin-1-one;

5-Chloro-2-[5-[2-(1-ethylpyrazole-4-carbonyl)-2,6-diazaspiro[3.3]heptan-6-yl]-3-pyridyl]-3,3-dimethyl-isoindolin-1-one;

5-Chloro-3,3-dimethyl-2-[5-[2-(4-methylpyridine-3-carbonyl)-2,6-diazaspiro[3.3]heptan-6-yl]-3-pyridyl]isoindolin-1-one;

2-[5-[2-(1-Ethylpyrazole-4-carbonyl)-2,6-diazaspiro[3.3]heptan-6-yl]-3-pyridyl]-3,3-dimethyl-1-oxo-isoindoline-5-carbonitrile;

2-Methoxy-7,7-dimethyl-6-[5-[2-(1-methylpyrazole-4-carbonyl)-2,6-diazaspiro[3.3]heptan-6-yl]-3-pyridyl]pyrrolo[3,4-b]pyridin-5-one;

5'-Chloro-2'-[5-[2-(1-methylpyrazole-4-carbonyl)-2,6-diazaspiro[3.3]heptan-6-yl]-3-pyridyl]spiro[cyclopropane-1,3'-isoindoline]-1'-one;

5-Chloro-3,3-dimethyl-2-[5-[7-(1-methylpyrazole-4-carbonyl)-2,7-diazaspiro[3.5]nonan-2-yl]-3-pyridyl]isoindolin-1-one;

5-Chloro-2-[5-[7-(1-ethylpyrazole-4-carbonyl)-2,7-diazaspiro[3.5]nonan-2-yl]-3-pyridyl]-3,3-dimethyl-isoindolin-1-one;

5-Chloro-3,3-dimethyl-2-[5-[2-(1-methylpyrazole-4-carbonyl)-2,7-diazaspiro[3.5]nonan-7-yl]-3-pyridyl]isoindolin-1-one;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the persons skilled in the art such as e.g. chiral chromatography or crystallization. The substituents and indices used in the following description of the processes have the significance given herein.

The following abbreviations are used in the present text: AcOH=acetic acid, BOC=t-butyloxycarbonyl, BuLi=butyllithium, CDI=1,1-carbonyldiimidazole, DCM=dichloromethane, DBU=2,3,4,6,7,8,9,10-octahydro-pyrimido[1,2-a]azepine, DCE=1,2-dichloroethane, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, Et$_2$O=diethylether, Et$_3$N=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=iPr$_2$NEt=N-ethyl diisopropylamine, IPC=in process control, LAH=lithium aluminium hydride, LDA=lithium diisopropylamide, LiBH$_4$=lithium borohydride, MeOH=methanol, NaBH$_3$CN, sodium cyanoborohydride, NaBH$_4$=sodium borohydride, NaI=sodium iodide, Red-Al=sodium bis(2-methoxyethoxy) aluminium hydride, RT=room temperature, TBDMSCl=t-butyldimethylsilyl chloride, TFA=trifluoroacetic acid, THF=tetrahydrofuran, quant=quantitative.

Halogen or triflate, preferably iodo substituted pyridine compounds 2 or 8 react with aryl lactams 1 in solvents like 1,4-dioxane, in the presence of copper (I) iodide, potassium or cesium carbonate or potassium phosphate, a chelating 1,2-diamino compound like N,N'-dimethylethylenediamine or trans-1,2-diamino-cyclohexane or a chelating beta keto ester compound like 2-isobutyryl-cyclohexanone, at elevated temperatures, optionally with the aid of microwave heating to form lactam substituted heterocyclic compounds 3 and 5 as described in Scheme 1a and Scheme 1b (step a). Amino compounds 4 or 6 (compounds which are known or can be readily prepared by methods known in the art) react with substituted pyridine compounds 3 under similar conditions as used in step a (step b), or preferably by using 'Buchwald' conditions, e.g. using catalysts like Pd(OAc)$_2$ and chelating ligands like Xanphos in the presence of a base like t-BuONa in solvents like dioxane at elevated temperature giving compounds 5 or 7. Compounds 5 with R$^{101}$ being a protecting group, e.g. the Boc group, can then be converted into compounds 7 by removal of the protecting group R$^{101}$ and reaction with a suitable activated carboxyl or sulfonyl compound (steps c, d; Schemes 1a and 1b).

Scheme 1a

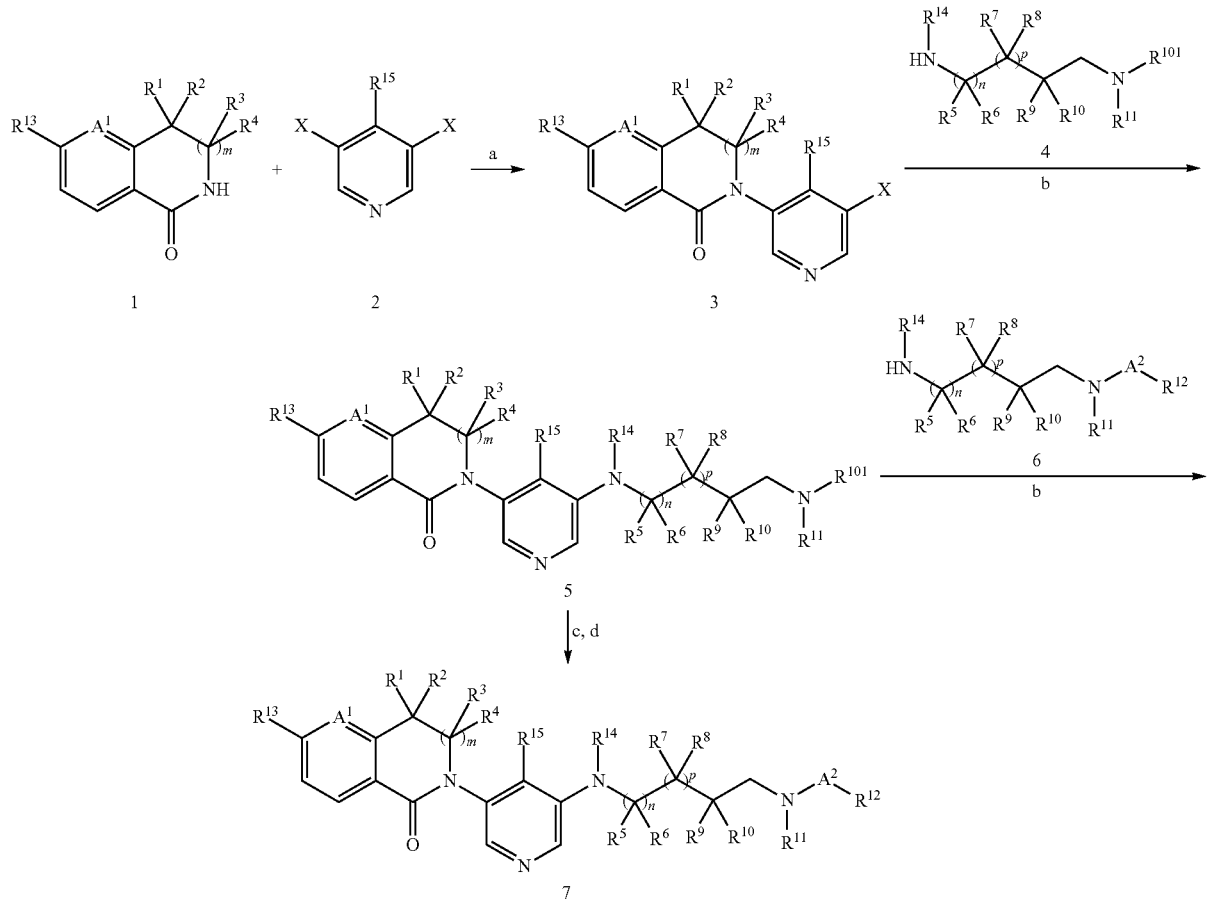

X is halogen or OSO₂CF₃
R¹⁰¹ is a suitable protecting group

Scheme 1b

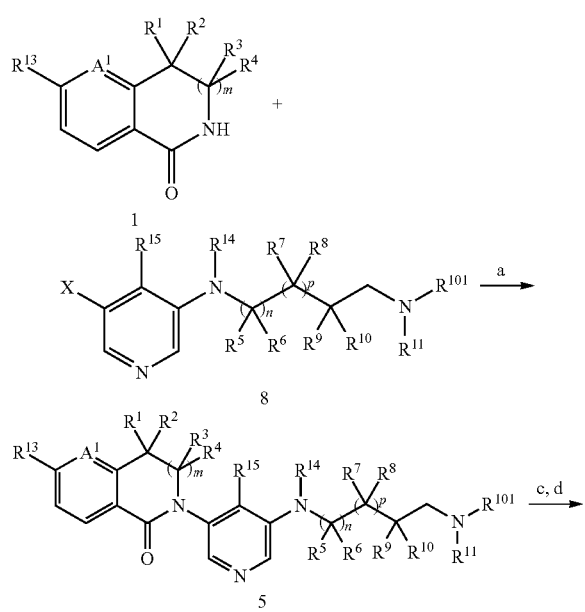

X is halogen or OSO₂CF₃
R¹⁰¹ is a suitable protecting group or A²—R¹²

Carbamates 101 (Scheme 2a) react with polyphosphoric acid at elevated temperature (e.g. 100-180° C.) to form lactam derivatives 102 (step a). Trifluoroacetamides 103 can be cyclized to 2,2,2-trifluoro-ethanone compounds 104 by treatment with paraformaldehyde in a mixture of concentrated sulfuric acid and acetic acid preferably around room temperature (step b). Removal of the trifluoroactyl group by treatment with e.g. potassium hydroxide in a solvent like ethanol at temperatures around room temperature gives secondary amino compounds 105 (step c). Oxidation of secondary amino compounds 105 e.g. with iodoso benzene and potassium bromide preferably in water gives lactam compounds 102 (step d). Reaction of compounds 106

(Scheme 2b) with a Grignard reagent R¹MgX in a solvent like THF preferably around 0° C. gives adducts 107 (step e). Subsequent treatment with triethylsilane and boron trifluoride etherate in a solvent like dichloromethane and in a temperature range preferably between −25° C. and RT gives compounds 108 (step f). Introduction a methoxybenzyl protecting group into compounds 109 (e.g. by treatment with sodium bis(trimethylsilyl)amide and 1-bromomethyl-4-methoxy-benzene in THF between 0° C. and RT) gives protected compounds 110 (step g); similarly, a methoxybenzyl protecting group can be introduced into compounds 108. Alternatively, compounds 110 can be obtained from halomethyl compounds 115 by reaction with p-methoxy-benzylamine in solvents like THF around RT (step m). Treatment of compounds 108 carrying an additional methoxybenzyl protecting group or compounds 110 with a base like sodium hydride in a solvent like THF and then with an alkyl halide, mesylate or tosylate preferably between RT and the reflux temperature of the solvent gives compounds 111 with one or both R¹ and R² groups different from hydrogen (step h). Alternatively, treatment of compounds 108 carrying an additional methoxybenzyl protecting group or compounds 110 with a base like NaH, LDA or LiHMDS in solvents like DMF, tetrahydrofuran or 1,2-dimethoxyethane and then with one or sequentially with two different alkyl halides, mesylates or tosylates preferably between −78° C. and the reflux temperature of the solvent gives compounds 111 with structurally different or structurally identical R¹ and R² groups (step h). Removal of the protecting group, e.g. by treatment with trifluoroacetic acid at elevated temperature gives compounds 112 (step i). Treatment of compounds 110 with a base like sodium hydride in a solvent like THF and then with an alpha, omega dihaloethane e.g. 1,2-dibromoethane, preferably between RT and the reflux temperature of the solvent gives spiro compounds 113 (step k) and after subsequent removal of the protecting group, spiro compounds 114 (step l).

Alternatively (Scheme 2c), compounds 117 with R¹ and R² being alkyl groups can be obtained from cyano compounds 116 and suitable Grignard reagents, either by addition of two different reagents sequentially or a single Grignard reagent in excess (to obtain compounds with identical R¹ and R²) preferably in the presence of titanium tetra-isopropoxide in solvents like THF preferably in a temperature range between 0° C. and RT (step n). Compounds 117 with R¹=H and R² being an alkyl group can be obtained from cyano compounds 116 and suitable Grignard reagents in solvents like THF preferably in a temperature range between 0° C. and RT (step n) followed by reduction of the imine formed with sodium borohydride in e.g. methanol around RT (step n). Compounds 119 are obtained from compounds 117 by reaction first with ethylmagnesium bromide and titanium tetra-isopropoxide in solvents like THF preferably in a temperature range between −78° C. and RT followed by treatment with BF₃-Et₂O (step p). Compounds 117 and 119 undergo ring closure by reaction with catalysts like dichloro[1,1'-bis(diphenylphosphino)-ferrocene]palladium(II) in solvents like DMF in the presence of a base like iPr₂NEt preferably in a temperature range between about 100° C. and 150° C. in an autoclave in the presence of carbon monoxide to form compounds 118 and 120 (step o).

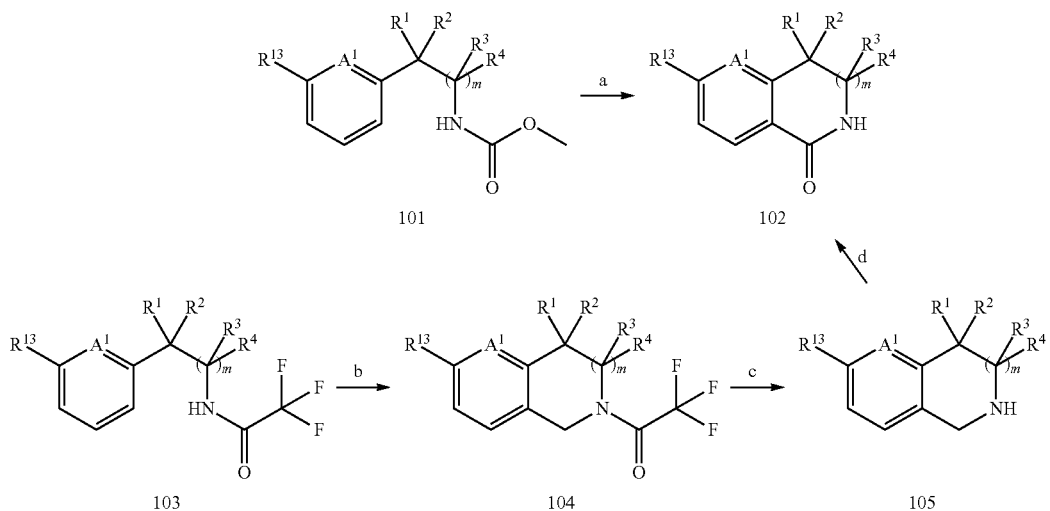

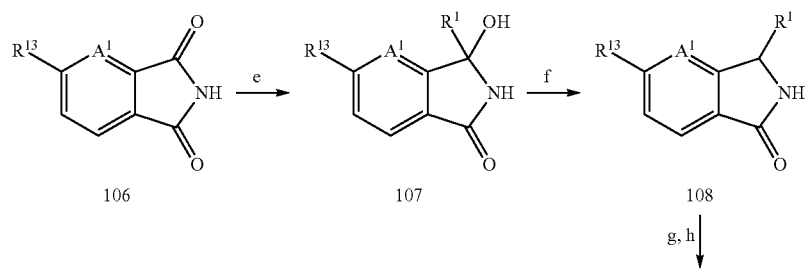

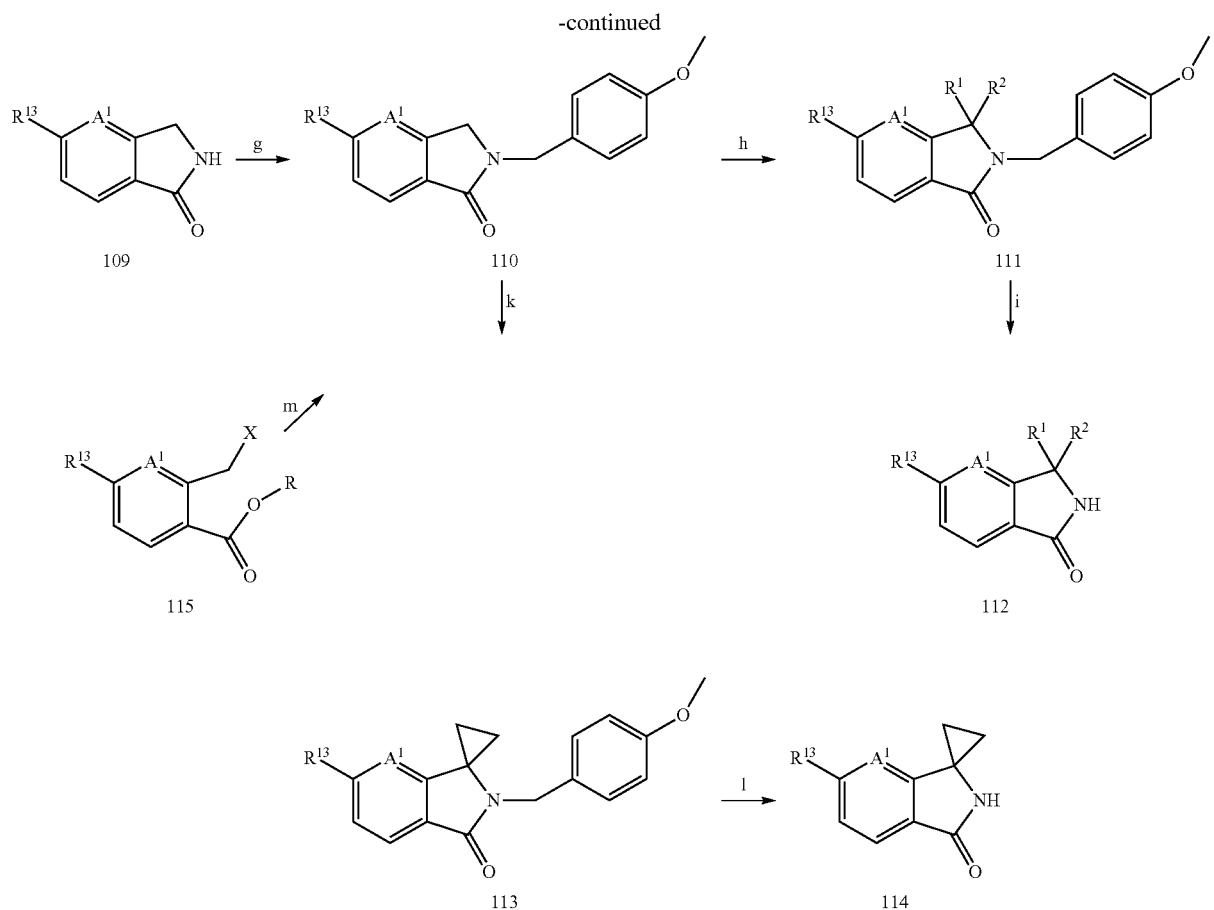
X is halogen or OSO₂CF₃
R is alkyl
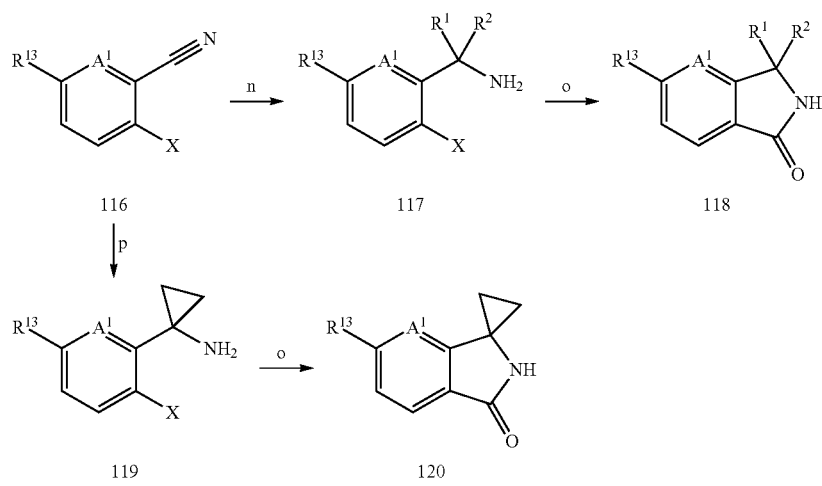
Scheme 2c
X is halogen or OSO₂CF₃
Halogen or triflate substituted compounds 8 can be prepared by reaction of amino compounds 4 with di-halo or di-triflate substituted pyridines 2 using conditions as described in Schemes 1 (step a), (Scheme 3).

Scheme 3

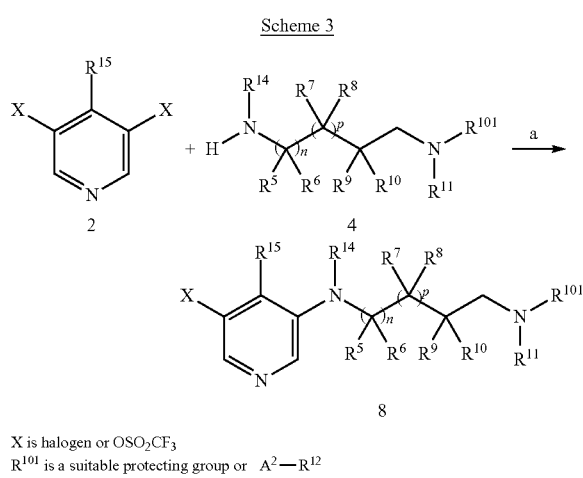

X is halogen or OSO$_2$CF$_3$
R$^{101}$ is a suitable protecting group or  A$^2$—R$^{12}$ Also an embodiment of the present invention is a process to prepare a compound of formula (I) as defined above comprising a) the reaction of a compound of formula (II) in the presence of a compound of formula (III);

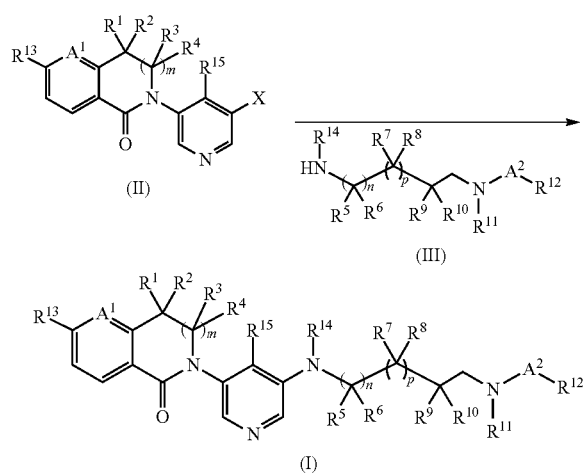

or b) the reaction of a compound of formula (IV) in the presence of a compound of formula (V);

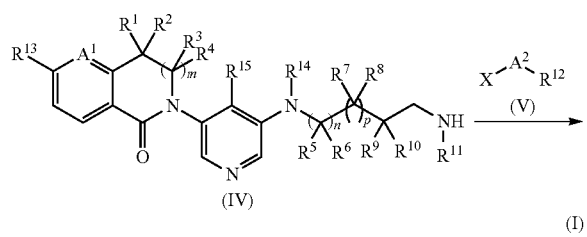

wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, A$^1$, A$^2$ m, n and p are as described herein and X in step a) is halogen or triflate and is halogen in step b).

In particular, in step a), in the presence of copper (I) iodide, potassium or cesium carbonate or potassium phosphate, a chelating 1,2-diamino compound like N,N'-dimethylethylenediamine or trans-1,2-diamino-cyclohexane or a chelating beta keto ester compound like 2-isobutyryl-cyclohexanone, at elevated temperatures, preferable with the aid of microwave heating and in solvents like 1,4-dioxane.

In particular, in step b), in the presence of a base, such as triethylamine, in a solvent such as dichloromethane at a temperature comprise between −10° C. and RT.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

The present invention also relates to the use of a compound according to formula (I) as described herein for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of diabetic nephropathy.

The present invention also relates to the use of a compound according to formula (I) as described herein for the treatment or prophylaxis of kidney or heart fibrosis.

The present invention also relates to the use of a compound according to formula (I) as described herein for the treatment or prophylaxis of chronic kidney disease.

The present invention also relates to the use of a compound according to formula (I) as described herein for the treatment or prophylaxis of congestive heart failure.

The present invention also relates to the use of a compound according to formula (I) as described herein for the treatment or prophylaxis of hypertension.

The present invention also relates to the use of a compound according to formula (I) as described herein for the treatment or prophylaxis of primary aldosteronism.

A particular embodiment of the present invention is a compound according to formula (I) as described herein for the treatment or prophylaxis of chronic kidney disease, congestive heart failure, hypertension, primary aldosteronism and Cushing syndrome.

Also a particular embodiment of the present invention is a compound according to formula (I) as described herein for the treatment or prophylaxis of diabetic nephropathy.

Another particular embodiment of the present invention is a compound according to formula (I) as described herein for the treatment or prophylaxis of kidney or heart fibrosis.

Also a particular embodiment of the present invention is a compound according to formula (I) as described herein for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein for the preparation of a medicament for the treatment or prophylaxis of chronic kidney disease, congestive heart failure, hypertension, primary aldosteronism and Cushing syndrome.

The present invention also relates to the use of a compound according to formula (I) as described herein for the preparation of a medicament for the treatment or prophylaxis of diabetic nephropathy.

The present invention also relates to the use of a compound according to formula (I) as described herein for the preparation of a medicament for the treatment or prophylaxis of kidney or heart fibrosis.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein for the preparation of a medicament for the treatment or prophylaxis of congestive heart failure.

Also an embodiment of the present invention is the use of a compound according to formula (I) as described herein for the preparation of a medicament for the treatment or prophylaxis of hypertension.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein.

Also an object of the invention is a method for the treatment or prophylaxis of diabetic nephropathy, which method comprises administering an effective amount of a compound according to formula (I) as described herein.

Also an object of the invention is a method for the treatment or prophylaxis of kidney or heart fibrosis, which method comprises administering an effective amount of a compound according to formula (I) as described herein.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein.

Also an embodiment of the present invention is a compound of formula (I) as described herein, when manufactured according to any one of the described processes.

Assay Procedures

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynmolgus CYP11B1 or cynomolgus CYP11B2 enzyme activity. Importantly the identified cell line G-402 expresses co-factors (adrenodoxin and adrenodoxin reductase) important for the activity of the CYP11 family and no relevant enzyme activity of the CYP11 family (in comparison to H295R cells) was detected in these cells. Therefore the G-402 cell line is uniquely suited as a host cell for the ectopic expression of enzymes from the CYP11 family.

G-402 cells can be obtained from ATCC (CRL-1440) and were originally derived from a renal leiomyoblastoma.

The expression plasmids contains the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp11B2) or 11-Deoxycortisol (Cyp11B1) as a substrate.

G-402 cells expressing CYP11 constructs were established as described above and maintained in McCoy's 5a Medium Modified, ATCC Catalog No. 30-2007 containing 10% FCS and 400 µg/ml G418 (Geneticin) at 37° C. under an atmosphere of 5% CO2/95% air. Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations (x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein, A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp11B2 enzyme activity was tested in presence of 1 µM Deoxycorticosterone and variable amounts of inhibitors; Cyp11B1 enzyme activity was tested in presence of 1 µM Deoxycortisol and variable amounts of inhibitors.

F. Hoffmann-La Roche AG, CH-4070 Basel, Switzerland

Case: 31601

| Example | EC50 human CYP11B2 nM | EC50 human CYP11B1 nM |
|---|---|---|
| 1 | 0.002 | 11.3428 |
| 2 | 0.003 | 11.0992 |
| 3 | 0.0083 | 11.0867 |
| 4 | 0.0099 | 1.1022 |
| 5 | 0.145 | 15.6621 |
| 6 | 0.0117 | 7.9433 |
| 7 | 0.0138 | 25.7471 |
| 8 | 0.1119 | >30 |
| 9 | 0.009 | 24.3739 |
| 10 | 0.0155 | 25.5513 |
| 11 | 0.0252 | 4.7581 |
| 12 | 0.1914 | >30 |
| 13 | 0.0278 | 26.4325 |
| 14 | 0.0407 | 21.0354 |
| 15 | 0.0205 | 18.9125 |
| 16 | 0.0827 | 29.2555 |
| 17 | 0.901 | 33.1839 |
| 18 | 0.0078 | 16.6651 |
| 19 | 0.0029 | 7.6917 |
| 20 | 0.0195 | 19.9885 |
| 21 | 0.2935 | >30 |
| 22 | 0.0063 | 37.3628 |
| 23 | 0.0073 | 11.9583 |
| 24 | 0.0449 | 17.1715 |
| 25 | 0.102 | 17.1715 |
| 26 | 0.0775 | 35.5314 |
| 27 | 0.1044 | 13.9735 |
| 28 | 0.0577 | 0.64 |
| 29 | 0.0748 | >30 |
| 30 | 0.0456 | 3.7501 |
| 31 | 0.154 | 6.4332 |
| 32 | 0.0149 | 5.3659 |
| 33 | 0.0497 | 1.7462 |
| 34 | 0.097 | 9.5549 |
| 35 | 0.3329 | 29.458 |
| 36 | 0.0457 | 30.9852 |
| 37 | 0.0754 | 16.102 |
| 38 | 0.0268 | 2.3171 |
| 39 | 0.0282 | 9.6823 |
| 40 | 0.0542 | 12.0285 |
| 41 | 0.1094 | 28.4076 |
| 42 | 0.0102 | 1.0543 |
| 43 | 0.018 | 18.0311 |
| 44 | 0.0907 | 17.9629 |
| 45 | 0.068 | 2.0882 |
| 46 | 0.0383 | 3.8633 |
| 47 | 0.5045 | 8.3061 |
| 48 | 0.2395 | >30 |
| 49 | 0.1106 | 5.0718 |
| 50 | 0.0248 | 16.8103 |
| 51 | 0.0101 | 13.7852 |
| 52 | 0.0082 | 22.0816 |
| 53 | 0.0459 | 14.5662 |
| 54 | 0.0084 | 22.0026 |
| 55 | 0.0071 | 20.6861 |
| 56 | 0.0032 | 18.8349 |
| 57 | 0.049 | 9.724 |
| 58 | 0.0038 | 9.6433 |
| 59 | 0.0014 | 0.8188 |
| 60 | 0.0024 | 0.8916 |
| 61 | 0.0024 | 2.1104 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 50 uM, more particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein are inhibitors of CYP11B2. The compounds of formula (I) or their pharmaceutically acceptable salts and esters herein display also variable inhibition of CYP11B1 but present an improved selectivity towards CYP11B2 versus CYP11B1. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), vascular conditions, endothelial dysfunction, baroreceptor dysfunction, renal conditions, liver conditions, fibrotic diseases, inflammatory conditions, retinopathy, neuropathy (such as peripheral neuropathy), pain, insulinopathy, edema, edematous conditions, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, cardiac fibrosis, hypertrophic cardiomyopathy, impaired arterial compliance, impaired diastolic filling, ischemia, left ventricular hypertrophy, myocardial and vascular fibrosis, myocardial infarction, myocardial necrotic lesions, cardiac arrhythmias, prevention of sudden cardiac death, restenosis, stroke, vascular damage.

Renal conditions include acute and chronic renal failure, nephropathy, end-stage renal disease, diabetic nephropathy, decreased creatinine clearance, decreased glomerular filtration rate, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, proteinuria, reduced renal blood flow, renal arteriopathy, swelling and proliferation of intracapillary (endothelial and mesangial) and/or extracapillary cells (crescents).

Renal conditions also include glomerulonephritis (such as diffuse proliferative, focal proliferative, mesangial proliferative, membranoproliferative, minimal change membranous glomerulonephritis), lupus nephritis, non-immune basement membrane abnormalities (such as Alport syndrome), renal fibrosis and glomerulosclerosis (such as nodular or global and focal segmental glomerulosclerosis).

Liver conditions include, but are not limited to, liver steatosis, nonalcoholic steatohepatitis, liver cirrhosis, liver ascites, hepatic congestion and the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, liver ascites, splenic congestion, respiratory or lung congestion, and the like.

Insulinopathies include, but are not limited to, insulin resistance, Type I diabetes mellitus, Type II diabetes mellitus, glucose sensitivity, pre-diabetic state, pre-diabetes, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In particular embodiment, the cardiovascular condition is treatment-resistant hypertension.

In another embodiment, the cardiovascular condition is heart failure.

In another embodiment, the cardiovascular condition is left ventricular hypertrophy.

In another embodiment, the cardiovascular condition is congestive heart failure, more particularly in patients with preserved left ventricular ejection fraction.

In another embodiment, the cardiovascular condition is stroke.

In another embodiment, the compounds of formula (I) or their pharmaceutically acceptable salts and esters can be used for the treatment or prophylaxis renal condition.

In another embodiment, the renal condition is nephropathy.

In another embodiment, the renal condition is auto-immune glomerulonephritis.

In another embodiment, the chronic kidney disease is diabetic nephropathy.

In another embodiment, the fibrotic disease is kidney or heart fibrosis.

In another embodiment, the compounds of formula (I) or their pharmaceutically acceptable salts and esters can be used for the treatment or prophylaxis Type II diabetes mellitus.

In another embodiment, the compounds of formula (I) or their pharmaceutically acceptable salts and esters can be used for the treatment or prophylaxis Type I diabetes mellitus.

In another embodiment, the compounds of formula (I) or their pharmaceutically acceptable salts and esters can be used for the treatment or prophylaxis of diabetic retinopathy.

The invention is illustrated hereinafter by Examples, which have no limiting character.

In case the preparative examples are obtained as a mixture of enantiomers, the pure enantiomers can be separated by methods described herein or by methods known to the persons skilled in the art, such as e.g. chiral chromatography or crystallization.

EXAMPLES

All examples and intermediates were prepared under argon atmosphere if not specified otherwise.

Intermediate A-1

6-Chloro-3,4-dihydro-2H-isoquinolin-1-one

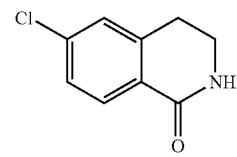 [SMILES: O=C1NCCc2cc(Cl)ccc21]

[A] [2-(3-Chloro-phenyl)-ethyl]-carbamic acid methyl ester

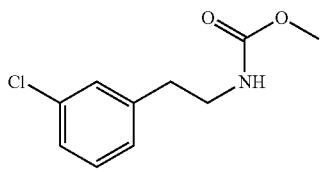

At 0° C., methyl chloroformate (4.6 g, 48 mmol) was added drop wise to a solution of 2-(3-chloro-phenyl)-ethyl-amine (5.0 g, 32 mmol) and Et$_3$N (6.4 g, 64 mmol) in DCM (100 mL). After the addition, the mixture was stirred at room temperature for 0.5 hours. The organic layer was washed with water (3×30 mL), 1N HCl (20 mL) and brine (30 mL), dried over anhy. Na$_2$SO$_4$, filtered and concentrated in vacuo. After vacuum drying, the title compound was obtained (6.49 g, 95%) as a white solid. MS: 214.1 (M+H)$^+$.

[B] 6-Chloro-3,4-dihydro-2H-isoquinolin-1-one

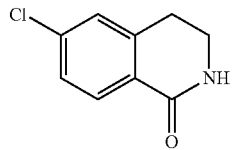

Under N$_2$ protection, a mixture of [2-(3-chloro-phenyl)-ethyl]-carbamic acid methyl ester (5.0 g, 23.4 mmol) and PPA (polyphosphoric acid) (20 g) in a 250 mL round-bottom flask was vigorously stirred at 120° C. for 2 hours. After cooling to room temperature, the reaction mixture was treated with ice-water and aqueous ammonia solution to adjust the pH to 8. Then, the mixture was extracted with EtOAc, and the organic layer was washed with brine, dried over anhy. Na$_2$SO$_4$ and filtered. After removal of solvent under reduced pressure, the crude product obtained was further washed with ethyl ether to give title compound (1.66 g, 39%) as a white solid. MS: 182.0 (M+H)$^+$.

Intermediate A-2

5-Chloro-3-methyl-2,3-dihydro-isoindol-1-one

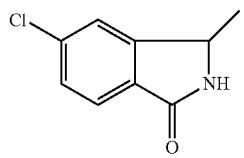

[A] 1-(2-Bromo-5-chloro-phenyl)-ethylamine

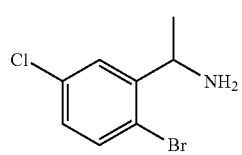

To a stirred solution of 2-bromo-5-chlorobenzonitrile (80 g, 370 mmol) in THF (1000 mL) at 0° C. was added MeMgBr (370 mL, 1110 mmol) drop wise. The reaction mixture was stirred at 0-5° C. for 5 hours before MeOH (500 mL) was added drop wise. After the solution was stirred for another 15 min, NaBH$_4$ (28 g, 740 mmol) was added carefully and the resulting mixture was stirred at room temperature for 16 hours. The reaction solution was then poured into water, exacted with EtOAc (3×). The combined organic layers were dried over anhy. Na$_2$SO$_4$, filtered and concentrated in vacuo to give a crude product, which was purified by silica gel flash chromatography (petroleum ether: EtOAc=3:1) to afford title compound (30 g, 35%) as yellowish oil. MS: 235.5 (M+H)$^+$.

[B] 5-Chloro-3-methyl-2,3-dihydro-isoindol-1-one

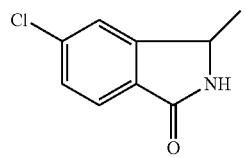

A mixture of 1-(2-bromo-5-chlorophenyl)ethanamine (30 g, 127.9 mmol), Pd(dppf)Cl$_2$ (3.2 g, 12.79 mmol), and DIPEA (49.5 g, 383.7 mmol) in DMF (1.2 L) was stirred in an autoclave under 2 MPa of CO at 130° C. for 24 hours. After it was cooled to room temperature, the reaction mixture was diluted with EtOAc (500 mL). The organic layer was washed with brine, filtered, and concentrated in vacuo to give a crude product which was purified by silica gel flash chromatography (petroleum ether:EtOAc=3:1) to give the title compound (5.2 g, 23%) as a brown solid. MS: 181.6 (M+H)$^+$.

Intermediate A-3

5-Chloro-3,3-dimethyl-2,3-dihydro-isoindol-1-one

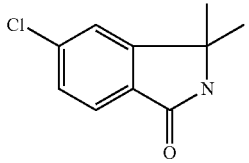

[A] 1-(2-Bromo-5-chloro-phenyl)-1-methyl-ethyl-amine

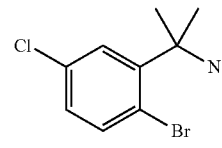

To a stirred solution of 2-bromo-5-chloro-benzonitrile (10 g, 46 mmol) in THF (200 mL) at 0° C., was added MeMgBr (77 mL, 230 mmol) drop wise. The reaction mixture was allowed to warm up to room temperature and stirred for 2 hours. Ti(Oi-Pr)$_4$ (13 g, 46 mmol) was added and the solution was stirred for another 16 hours before it was quenched with aq. HCl solution and washed with EtOAc. The aqueous phase was adjusted to pH~10 with aq. NaOH solution, and exacted with EtOAc (3×). The combined organic layers were concentrated to give a crude title product (3.8 g, 33%) as oil, which was used directly in the next step without further purification. MS: 249.30 (M+H)$^+$.

[B]
5-Chloro-3,3-dimethyl-2,3-dihydro-isoindol-1-one

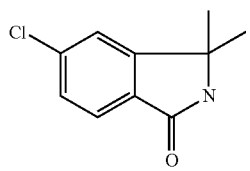

A mixture of 1-(2-bromo-5-chloro-phenyl)-1-methyl-ethylamine (3.8 g, 15.3 mmol), Pd(dppf)Cl$_2$ (0.4 g, 0.55 mmol) and DIPEA (6 g, 45.9 mmol) in DMF (20 mL) was stirred in an autoclave under 2 MPa of CO at 130° C. for 16 hours. After it was cooled to room temperature, the reaction mixture was diluted with EtOAc (300 mL). The organic layer was washed with brine (80 mL×2), filtered, and concentrated in vacuo to give a crude product which was purified by silica gel flash chromatography to give the title compound (1.13 g, 38%) as a brown solid. MS: 195.70 (M+H$^+$)

Intermediate A-4

3,3-Dimethyl-1-oxo-2,3-dihydro-1H-isoindole-5-carbonitrile

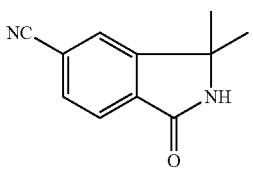

[A] 4-Bromo-2-methyl-benzoic acid methyl ester

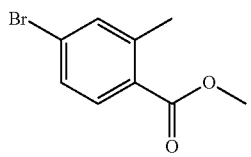

To a solution of 4-bromo-2-methyl-benzoic acid (30.0 g, 0.14 mol) in 115 mL of methanol was added thionyl chloride (20.25 mL, 0.28 mol) slowly and the reaction mixture was stirred at 70° C. for 2 hours before it was concentrated to afford a crude product which was then purified by silica gel flash chromatography to give the title compound (30.03 g, 93.6%) as a solid.

[B] 4-Cyano-2-methyl-benzoic acid methyl ester

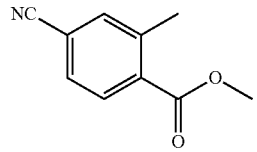

A mixture of 4-bromo-2-methyl-benzoic acid methyl ester (26.0 g, 113.5 mmol) and CuCN (12.48 g, 140.7 mmol) was heated at 180° C. for 5 hours before it was poured into ice-water. The solid precipitate was collected by vacuum filtration to give a crude product which was then purified by silica gel flash chromatography to afford the title compound (12.53 g, 63%) as a solid.

[C] 2-Bromomethyl-4-cyano-benzoic acid methyl ester

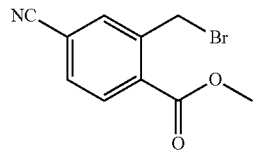

A mixture of 4-cyano-2-methyl-benzoic acid methyl ester (12.5 g, 71.35 mmol), NBS (12.7 g, 71.35 mmol) and di-benzoyl peroxide (BPO) (0.8 g, 3.28 mmol) in CCl$_4$ (200 mL) was heated to reflux temperature for 3 hours. After it was cooled to room temperature, the reaction mixture was filtered. The filtrate was concentrated in vacuo to give a crude product (18.2 g) which was used in the next step reaction without further purification.

[D] 2-(4-Methoxy-benzyl)-1-oxo-2,3-dihydro-1H-isoindole-5-carbonitrile

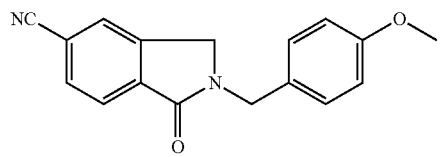 [SMILES: COc1ccc(CN2Cc3cc(C#N)ccc3C2=O)cc1]

To a solution of 2-bromomethyl-4-cyano-benzoic acid methyl ester (18.1 g, 71.24 mmol) in THF (300 mL) was added PMBNH$_2$ (23.4 g, 178.1 mmol) at 0° C. and the reaction mixture was stirred at room temperature for 16 hours. After vacuum filtration, the filtrate was concentrated in vacuo. The residue obtained was re-dissolved in EtOAc and washed with water and brine. The organic layer was dried over anhy. Na$_2$SO$_4$, filtered, and concentrated in vacuo to give a crude product which was purified by silica gel flash chromatography (11.69 g, 56.0%) as a solid.

[E] 2-(4-Methoxy-benzyl)-3,3-dimethyl-1-oxo-2,3-dihydro-1H-isoindole-5-carbonitrile

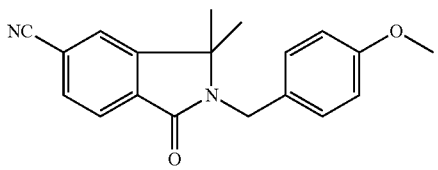 [SMILES: COc1ccc(CN2C(=O)c3ccc(C#N)cc3C2(C)C)cc1]

To a solution of 2-(4-methoxy-benzyl)-1-oxo-2,3-dihydro-1H-isoindole-5-carbonitrile (11.6 g, 41.7 mmol) in THF (300 mL) was added NaH (8.34 g, 208.4 mmol, 60% in mineral oil) and the reaction mixture was stirred at room temperature for 1 hour before iodomethane (35.5 g, 250.1 mmol) was added. After the addition, the reaction mixture was stirred at 70° C. for 2 hours until all the starting material was consumed. After it was cooled to room temperature, satd. aq. NH$_4$Cl solution was added and the mixture was extracted with EtOAc (3×200 mL). The combined organic layers were dried over anhy. MgSO$_4$, filtered, and concentrated under reduced pressure to give a crude product which was purified by silica gel flash chromatography to afford the title compound (7.22 g, 56.5%) as a solid.

[F] 3,3-Dimethyl-1-oxo-2,3-dihydro-1H-isoindole-5-carbonitrile

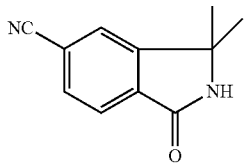

To a solution of 2-(4-methoxy-benzyl)-3,3-dimethyl-1-oxo-2,3-dihydro-1H-isoindole-5-carbonitrile (3.5 g, 11.42 mmol) in MeCN (70 mL) was added CAN (18.79 g, 34.27 mmol) in 30 mL of water at 0° C. The resulting reaction mixture was stirred at 0° C. for 1 hour until all the starting material was consumed. The reaction mixture was extracted between water and EtOAc and the combined organic layers were dried over anhy. MgSO$_4$, filtered, and concentrated under reduced pressure to give a crude product which was purified by silica gel flash chromatography to afford the title compound (1.06 g, 49.8%) as a solid.

Intermediate A-5

2-Methoxy-7,7-dimethyl-6,7-dihydro-pyrrolo[3,4-b]pyridin-5-one

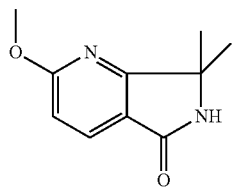

[A] 3-(Methoxycarbonyl)-2-methylpyridine 1-oxide

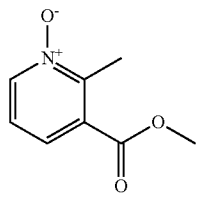

To a stirred solution of methyl-2-methylnicotinate (95 g, 629 mmol) in DCM (1.5 L) was added m-CPBA (119 g, 692 mmol) at 0° C. After the reaction mixture was stirred at room temperature for 16 hours, it was washed with a mixture of satd. aq. Na$_2$SO$_3$ and NaHCO$_3$ solution. The organic layer was then dried over anhy. Na$_2$SO$_4$, filtered, and concentrated in vacuo to give a crude product (60 g, 57%), which was used in the next step reaction without further purification.

[B] Methyl 2-(chloromethyl)nicotinate

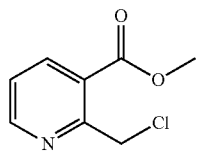

The crude material of 3-(methoxycarbonyl)-2-methyl-pyridine-1-oxide (35 g, 210 mmol) was added in small portion to POCl$_3$ (300 g) at room temperature. After the addition, the reaction mixture was refluxed for 3 hours before it was concentrated in vacuo. The residue was poured into ice-water, neutralized with aq. NaHCO$_3$ solution and extracted with EtOAc (125 mL×3). The combined organic layers were washed with brine, dried over anhy. Na$_2$SO$_4$, filtered, and concentrated in vacuo to afford a crude product which was then purified by silica gel flash chromatography to give title compound (12 g, 30%).

[C] 2-(Chloromethyl)-3-(methoxycarbonyl)pyridine 1-oxide

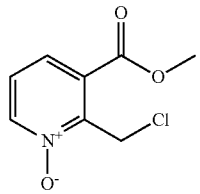

To a stirred solution of methyl-2-(chloromethyl)nicotinate (20 g, 108 mmol) in DCM (300 mL) was added m-CPBA (20.5 g, 119 mmol) at 0° C. After it was stirred at room temperature for 16 hours, the reaction mixture was washed with a mixture of satd. aq. Na$_2$SO$_3$ and NaHCO$_3$ solution. The organic layer was dried over anhy. Na$_2$SO$_4$, filtered, and concentrated in vacuo to give the crude title product (20 g, 92%), which was used in the next step reaction without further purification.

[D] Methyl 6-chloro-2-(chloromethyl)nicotinate

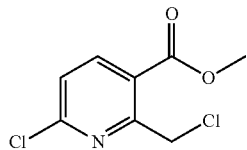

The crude material of 2-(chloromethyl)-3-(methoxycarbonyl)pyridine-1-oxide (20 g, 99.5 mmol) was added in small portion to POCl$_3$ (200 g) at room temperature. The mixture was refluxed for 3 hours before it was concentrated in vacuo. The residue was poured into ice-water, neutralized with satd. aq. NaHCO$_3$ solution, and extracted with EtOAc (125 mL×3). The combined organic layers were concentrated to give the crude title product (17 g, 78%), which was used in the next step reaction without further purification.

[E] 2-Chloro-6-(4-methoxybenzyl)-6,7-dihydro-5H-pyrrolo[3,4-b]pyridin-5-one

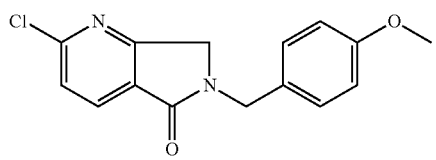 [SMILES: COc1ccc(CN2Cc3nc(Cl)ccc3C2=O)cc1]

To a stirred solution of crude material of methyl 6-chloro-2-(chloromethyl)nicotinate (10 g, 45.4 mmol) in THF (150 mL) was added PMBNH$_2$ (15.5 g, 113.5 mmol) at 0° C. The resulting reaction mixture was stirred at room temperature for 16 hours before it was concentrated under reduced pressure to give a crude product. After washing with MTBE (100 mL×3), the title compound was obtained (8.8 g, 67%) as a white solid. MS: 288.8 (M+H$^+$, 1Cl).

[F] 2-Chloro-6-(4-methoxy-benzyl)-7,7-dimethyl-6,7-dihydro-pyrrolo[3,4-b]pyridin-5-one

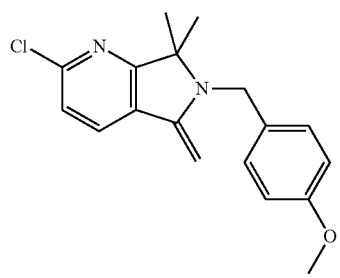 [SMILES: C=C1c2ccc(Cl)nc2C(C)(C)N1Cc1ccc(OC)cc1]

To a solution of 2-chloro-6-(4-methoxy-benzyl)-6,7-dihydro-pyrrolo[3,4-b]pyridin-5-one (5.8 g, 20.0 mmol) in THF (50 mL) was added sodium hydride (60% in mineral oil, 1.7 g, 42.0 mmol) at room temperature. The resulting reaction mixture was stirred for 30 min before iodomethane (6.0 g, 42.0 mmol) was added. After stirring at room temperature overnight, the mixture was quenched with water and extracted with EtOAc. The organic layer was then washed with brine, dried over anhy. Na$_2$SO$_4$, filtered and concentrated in vacuo to give the crude product which was then purified by silica gel flash chromatography (5% to 20% ethyl acetate in DCM). The title compound was obtained (3.8 g, 57%) as a white solid. MS: 316.2 (M+H$^+$).

[G] 2-Methoxy-6-(4-methoxy-benzyl)-7,7-dimethyl-6,7-dihydro-pyrrolo[3,4-b]pyridin-5-one

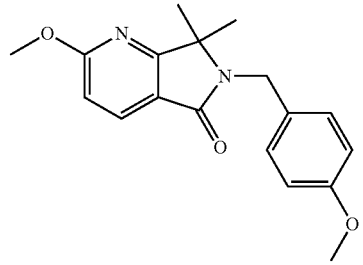 [SMILES: COc1ccc(CN2C(=O)c3ccc(OC)nc3C2(C)C)cc1]

To solution of 2-chloro-6-(4-methoxy-benzyl)-7,7-dimethyl-6,7-dihydro-pyrrolo[3,4-b]pyridin-5-one (3.15 g, 10 mmol) in DMF (30 mL) was added sodium methanolate (0.813 g, 15 mmol) at room temperature. The reaction mixture was stirred at room temperature for 4 hours before it was quenched with water and extracted with EtOAc. The organic layer was washed with brine, dried over anhy. Na$_2$SO$_4$, filtered and concentrated in vacuo to give title compound (2.8 g, 90%) as a solid. MS: 313.1 (M+H$^+$).

[H] 2-Methoxy-7,7-dimethyl-6,7-dihydro-pyrrolo[3,4-b]pyridin-5-one

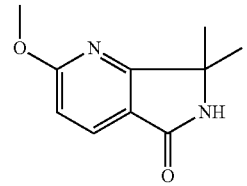

To solution of 2-methoxy-6-(4-methoxy-benzyl)-7,7-dimethyl-6,7-dihydro-pyrrolo[3,4-b]pyridin-5-one (0.31 g, 1.0 mmol) in CH$_3$CN (5 mL) was added ceric ammonium nitrate (1.64 g, 3.0 mmol) at room temperature. The reaction mixture was stirred at room temperature for 3 hours before water and EtOAc were added into the mixture. The organic layer was separated, dried over anhy. Na$_2$SO$_4$, filtered and concentrated in vacuo to give a crude product which was then purified by silica gel flash chromatography to give the title compound (0.12 g, 63%) as a solid. MS: 193.1 (M+H$^+$).

Intermediate A-6

5'-Chlorospiro[cyclopropane-1,3'-isoindoline]-1'-one

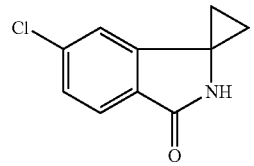 [SMILES: O=C1NC2(CC2)c2cc(Cl)ccc21]

[A] 1-(2-Bromo-5-chloro-phenyl)cyclopropanamine

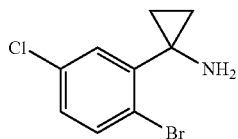 [SMILES: NC1(c2cc(Cl)ccc2Br)CC1]

To a stirred solution of 2-bromo-5-chlorobenzonitrile (10 g, 46 mmol) and Ti(Oi-Pr)$_4$ (16.64 mL, 55 mmol) in THF (200 mL) at −78° C. was added EtMgBr (138 mL, 138 mmol) drop wise. The reaction mixture was allowed to warm up to room temperature and stirred for 2 hours. BF$_3$-Et$_2$O (17.2 mL) was added, and the solution was stirred for another 16 hours before it was quenched with aq. HCl solution and washed with EtOAc. The aqueous phase was adjusted to pH ~10 with aq. NaOH solution, and exacted with EtOAc three times. The combined organic layers were concentrated to give a crude product which was purified by silica gel flash chromatography to afford title compound (2 g, 17.6%). MS: 246.7 (M+H$^+$, 1Cl) as oil.

[B] 5'-Chlorospiro[cyclopropane-1,3'-isoindoline]-1'-one

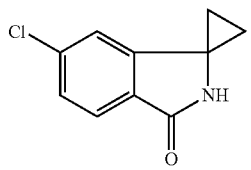 [SMILES: O=C1NC2(CC2)c2cc(Cl)ccc21]

A mixture of 1-(2-bromo-5-chlorophenyl)cyclopropanamine (2 g, 8.1 mmol), Pd(dppf)Cl$_2$ (0.2 g), DIPEA (3.1 g, 24.3 mmol) in DMF (20 mL) was stirred in an autoclave under 2 MPa of CO (g) at 130° C. for 16 hours. The reaction mixture was diluted with EtOAc (300 mL), and washed with brine. The organic layer was dried over anhy. Na$_2$SO$_4$, filtered, and concentrated under reduced pressure to give a crude product which was purified by silica gel flash chromatography to afford title compound (700 mg, 44.6%) as a yellow solid. MS: 193.8 (M+H$^+$, 1Cl).

Intermediate B-1

6-Chloro-2-[5-(2,6-diazaspiro[3.3]heptan-2-yl)-3-pyridyl]-3,4-dihydroisoquinolin-1-one

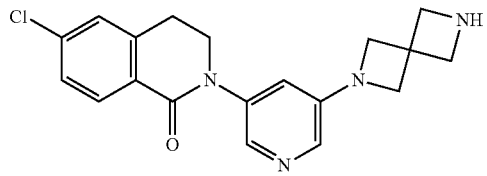 [SMILES: O=C1c2ccc(Cl)cc2CCN1c1cncc(N2CC3(CNC3)C2)c1]

[A] 6-Chloro-2-(5-iodo-3-pyridyl)-3,4-dihydroisoquinolin-1-one

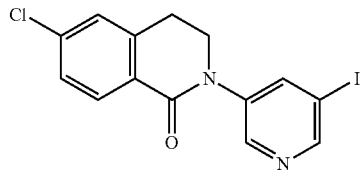 [SMILES: O=C1c2ccc(Cl)cc2CCN1c1cncc(I)c1]

A mixture of 6-chloro-3,4-dihydro-2H-isoquinolin-1-one (intermediate A-1, 380 mg, 2 mmol), 3,5-diiodopyridine (1.192 g, 3.6 mmol), CuI (152 mg, 0.8 mmol), (1S,2S)-cyclohexane-1,2-diamine (182.4 mg, 1.6 mmol) and K$_3$PO$_4$ (848 mg, 4 mmol) in dioxane (5 mL) was heated to reflux temperature for 3 hours. After cooling to room temperature, the mixture was poured into satd. aq. NaHCO$_3$ solution (20 mL) and extracted with EtOAc (3×30 mL). The combined organic layers were washed with brine, dried over anhy. Na$_2$SO$_4$, filtered and concentrated in vacuo to give a crude product, which was then purified by silica gel flash chromatography to afford the title compound (350 mg, 46%) as a white solid. MS: 385.1 (M+H$^+$).

[B] tert-Butyl6-[5-(6-chloro-1-oxo-3,4-dihydroisoquinolin-2-yl)-3-pyridyl]-2,6-diazaspiro[3.3]heptane-2-carboxylate

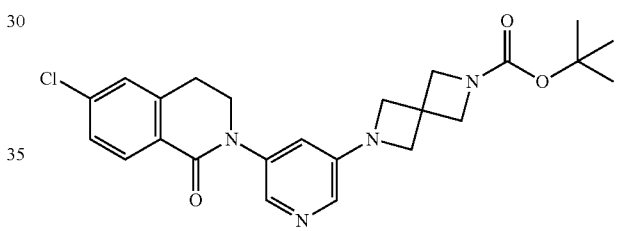

To a solution of 6-chloro-2-(5-iodo-3-pyridyl)-3,4-dihydroisoquinolin-1-one (480 mg, 1.25 mmol), tert-butyl 2,6-diazaspiro[3.3]heptane-2-carboxylate oxalate (500 mg, 1.74 mmol), Pd$_2$dba$_3$ (100 mg, 0.11 mmol), BINAP (120 mg, 0.19 mmol) and tBuONa (400 mg, 4.8 mmol) in toluene (10 mL) was added 10 drops of triethylamine. The resulting reaction mixture was then heated to 85° C. for 2 hours. After it was cooled to the room temperature, the mixture was poured into brine and extracted with DCM (3×10 mL). The combined organic layers were washed with brine, dried over anhy. Na$_2$SO$_4$, filtered and concentrated in vacuo to give a crude product, which was then purified by silica gel flash chromatography to afford the title compound (283 mg, 50%) as a brown solid. MS: 455.1 (M+H$^+$).

[C] 6-Chloro-2-[5-(2,6-diazaspiro[3.3]heptan-2-yl)-3-pyridyl]-3,4-dihydroisoquinolin-1-one

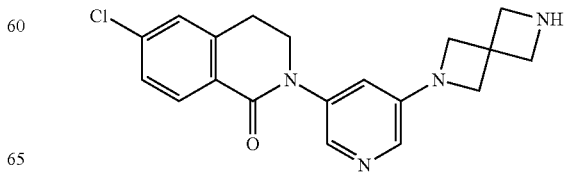

tert-Butyl 6-[5-(6-chloro-1-oxo-3,4-dihydroisoquinolin-2-yl)-3-pyridyl]-2,6-diazaspiro[3.3]heptane-2-carboxylate (454 mg, 1.0 mmol) was treated with TFA (5 mL) in DCM (5 mL) at 0° C. The reaction mixture was allowed to warm up to room temperature and stirred at room temperature for 1.5 hour before it was concentrated under reduced pressure to give desired titled compound (350 mg, 98%) as oil. MS: 355.1 (M+H$^+$). It was used directly in the next step without further purification.

Intermediate B-2

5-Chloro-2-[5-(2,6-diazaspiro[3.3]heptan-2-yl)-3-pyridyl]-3-methyl-isoindolin-1-one

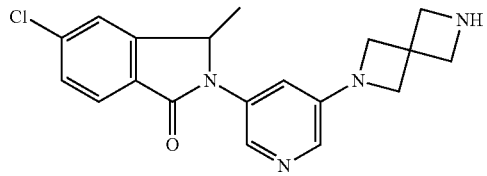 [SMILES: CC1c2cc(Cl)ccc2C(=O)N1c1cncc(N2CC3(CNC3)C2)c1]

[A] 2-(5-Bromo-3-pyridyl)-5-chloro-3-methyl-isoindolin-1-one

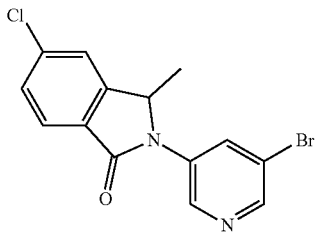 [SMILES: CC1c2cc(Cl)ccc2C(=O)N1c1cncc(Br)c1]

In a 75-mL sealed tube, 3-bromo-5-iodo-pyridine (4.3 g, 15 mmol), 2-(5-bromo-3-pyridyl)-5-chloro-3-methyl-isoindolin-1-one (intermediate A-2, 1.81 g, 10 mmol), CuI (1.4 g, 6 mmol), K$_3$PO$_4$ (4.24 g, 20 mmol) and (+)-(S,S)-1,2-diaminocyclohexane (0.7 mL, 6 mmol) were dissolved in dioxane (20 mL). The resulting reaction mixture was heated at 120° C. for 3 hours before it was poured into water (50 mL) and extracted with EtOAc (2×125 mL). The combined organic layers were washed with brine, dried over anhy. Na$_2$SO$_4$, filtered and concentrated in vacuo to give a crude product, which was purified by silica gel flash chromatography (0-60% EtOAc-hexane gradient) to afford the title compound (2.8 g, 83.1%) as a light yellow solid. MS: 337.1 & 339.1 (M+H$^+$).

[B] tert-Butyl 6-[5-(5-chloro-3-methyl-1-oxo-isoindolin-2-yl)-3-pyridyl]-2,6-diazaspiro[3.3]heptane-2-carboxylate

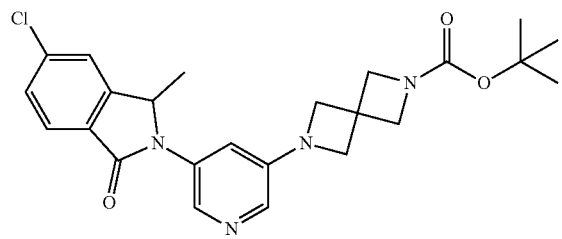 [SMILES: CC1c2cc(Cl)ccc2C(=O)N1c1cncc(N2CC3(CN(C(=O)OC(C)(C)C)C3)C2)c1]

A mixture of 2-(5-bromo-3-pyridyl)-5-chloro-3-methyl-isoindolin-1-one (674 mg, 2 mmol), tert-butyl 2,6-diazasprio[3.3]heptane-2-carb oxylateoxalate (870 mg, 3 mmol), Pd$_2$(dba)$_3$ (137 mg), BINAP (165 mg), t-BuONa (580 mg, 6 mmol) and TEA (1 mL, 7.2 mmol) in toluene (20 mL) were stirred at 110° C. for 12 hours. After cooling to room temperature, the reaction mixture was poured into water (20 mL) and extracted with EtOAc (2×100 mL). The combined organic layers were washed with brine, dried over anhy. Na$_2$SO$_4$, filtered and concentrated in vacuo to give a crude product, which was purified by silica gel flash chromatography (30-100% EtOAc-hexane gradient) to afford the title compound (800 mg, 88.9%) as a light yellow foam. MS: 455.2 (M+H$^+$).

[C] 5-Chloro-2-[5-(2,6-diazaspiro[3.3]heptan-2-yl)-3-pyridyl]-3-methyl-isoindolin-1-one

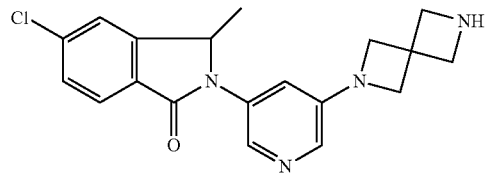 [SMILES: CC1c2cc(Cl)ccc2C(=O)N1c1cncc(N2CC3(CNC3)C2)c1]

A solution of tert-butyl 6-[5-(5-chloro-3-methyl-1-oxo-isoindolin-2-yl)-3-pyridyl]-2,6-diazaspiro[3.3]heptane-2-carboxylate (800 mg, 0.889 mmol) and TFA (2 mL) in DCM (5 mL) was stirred at room temperature for 2 hours before it was concentrated in vacuo to afford the crude title compound (900 mg) as light yellow oil. MS: 355.1 (M+H$^+$). It was used directly in the next step without further purification.

Intermediate B-3

5-Chloro-2-[5-(2,6-diazaspiro[3.3]heptan-2-yl)-3-pyridyl]-3,3-dimethyl-isoindolin-1-one

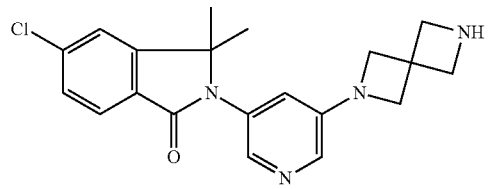 [SMILES: CC1(C)c2cc(Cl)ccc2C(=O)N1c1cncc(N2CC3(CNC3)C2)c1]

[A] 5-Chloro-2-(5-iodo-3-pyridyl)-3,3-dimethyl-isoindolin-1-one

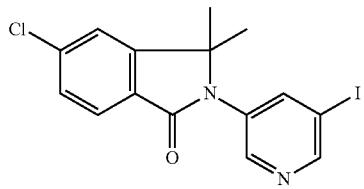 [SMILES: CC1(C)c2cc(Cl)ccc2C(=O)N1c1cncc(I)c1]

A mixture of 5-chloro-3,3-dimethyl-2,3-dihydro-isoindol-1-one (intermediate A-3, 2.5 g, 12.8 mmol), 3,5-diiodopyridine (8.7 g, 26.8 mmol), CuI (2.0 g, 10.2 mmol), (1S,2S)-cyclohexane-1,2-diamine (2.0 g, 20.9 mmol) and K₃PO₄ (6.3 g, 28.5 mmol) in dioxane (40 was heated at reflux temperature for 3 hours. After cooling to room temperature, the mixture was poured into satd. aq. NaHCO₃ solution (20 mL) and extracted with EtOAc (3×30 mL). The combined organic layers were washed with brine, dried over anhy. Na₂SO₄, filtered and concentrated in vacuo to give a crude product, which was then purified by silica gel flash chromatography to afford the title compound (2.5 g, 49%) as a white solid. MS: 399.0 (M+H⁺).

[B] tert-Butyl 6-[5-(6-chloro-1,1-dimethyl-3-oxo-isoindolin-2-yl)-3-pyridyl]-2,6-diazaspiro[3.3]heptane-2-carboxylate

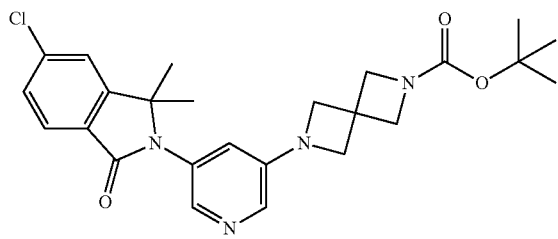 [SMILES: CC(C)(C)OC(=O)N1CC2(C1)CN(c1cncc(N3C(=O)c4ccc(Cl)cc4C3(C)C)c1)C2]

To a solution of 5-chloro-2-(5-iodo-3-pyridyl)-3,3-dimethyl-isoindolin-1-one (300 mg, 1.25 mmol), tert-butyl 2,6-diazaspiro[3.3]heptane-2-carboxylate oxalate (500 mg, 1.74 mmol), Pd₂dba₃ (100 mg, 0.11 mmol), BINAP (120 mg, 0.19 mmol) and tBuONa (400 mg, 4.8 mmol) in toluene (10 mL) was added 10 drops of triethylamine. The reaction mixture was the heated to 85° C. for 2 hours. After cooling to room temperature, the mixture was poured into brine and extracted with DCM (3×10 mL). The combined organic layers were washed with brine, dried over anhy. Na₂SO₄, filtered and concentrated in vacuo to give a crude product, which was then purified by silica gel flash chromatography to afford the title compound (460 mg, 52%) as a brown solid. MS: 469.1 (M+H⁺).

[C] 5-Chloro-2-[5-(2,6-diazaspiro[3.3]heptan-2-yl)-3-pyridyl]-3,3-dimethyl-isoindolin-1-one

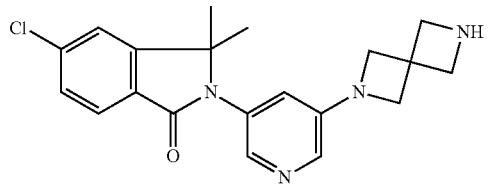 [SMILES: CC1(C)c2cc(Cl)ccc2C(=O)N1c1cncc(N2CC3(CNC3)C2)c1]

tert-Butyl-6-[5-(6-chloro-1,1-dimethyl-3-oxo-isoindolin-2-yl)-3-pyridyl]-2,6-diazaspiro[3.3]heptane-2-carboxylate (920 mg, 1.96 mmol) was treated with TFA (10 mL) in DCM (12 mL) at 0° C. The reaction mixture was allowed to warm up to room temperature and stirred at room temperature for 1.5 hours. The reaction mixture was concentrated under reduced pressure to give the titled compound as oil, which was used directly in the next step without further purification. MS: 369.1 (M+H⁺).

Intermediate B-4

2-[5-(2,6-Diazaspiro[3.3]heptan-2-yl)-3-pyridyl]-3,3-dimethyl-1-oxo-isoindoline-5-carbonitrile

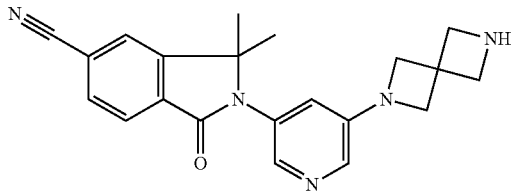 [SMILES: CC1(C)c2cc(C#N)ccc2C(=O)N1c1cncc(N2CC3(CNC3)C2)c1]

[A] 2-(5-Iodo-3-pyridyl)-3,3-dimethyl-1-oxo-isoindoline-5-carbonitrile

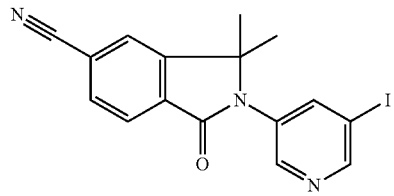 [SMILES: CC1(C)c2cc(C#N)ccc2C(=O)N1c1cncc(I)c1]

A solution of 3,3-dimethyl-1-oxo-isoindoline-5-carbonitrile (intermediate A-4, 650 mg, 3.5 mmol), 3,5-diiodopyridine (2.0 g, 6.0 mmol), CuI (200 mg, 1.05 mmol), (1S,2S)-cyclohexane-1,2-diamine (240 mg, 2.1 mmol) and K₃PO₄ (1.5 g, 7 mmol) in dioxane (8 mL) was heated at reflux temperature for 4 hours. After cooling to room temperature, the mixture was poured into satd. aq. NaHCO₃ solution (20 mL) and extracted with EtOAc (3×30 mL). The combined organic layers were washed with brine, dried over anhy. Na₂SO₄, filtered and concentrated in vacuo to give a crude product, which was then purified by silica gel flash chromatography to afford the title compound (350 mg, 26%) as a white solid. MS: 389.6 (M+H⁺).

[B] tert-Butyl 6-[5-(6-cyano-1,1-dimethyl-3-oxo-isoindolin-2-yl)-3-pyridyl]-2,6-diazaspiro[3.3]heptane-2-carboxylate

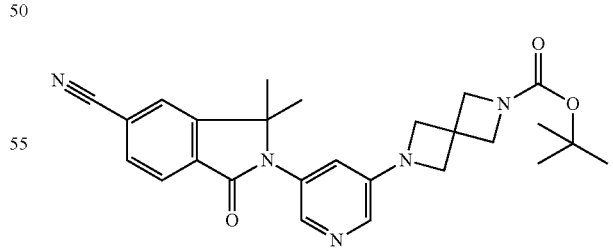

To a solution of 2-(5-iodo-3-pyridyl)-3,3-dimethyl-1-oxo-isoindoline-5-carbonitrile (561 mg, 1.44 mmol), tert-butyl 2,6-diazaspiro[3.3]heptane-2-carboxylate oxalate (500 mg, 1.74 mmol), Pd₂dba₃ (100 mg, 0.11 mmol), BINAP (120 mg, 0.19 mmol) and tBuONa (400 mg, 4.8 mmol) in toluene (10 mL) was added 10 drops of triethylamine. The reaction mixture was the heated to 100° C. for 3 hours. After cooling to room temperature, the mixture was poured into brine and extracted with EtOAc (3×10 mL). The combined organic layers were washed with brine, dried over anhy. Na$_2$SO$_4$, filtered and concentrated in vacuo to give a crude product, which was then purified by silica gel flash chromatography to afford the title compound (300 mg, 45%) as a brown solid. MS: 460.1 (M+H$^+$).

[C] 2-[5-(2,6-Diazaspiro[3.3]heptan-2-yl)-3-pyridyl]-3,3-dimethyl-1-oxo-isoindoline-5-carbonitrile

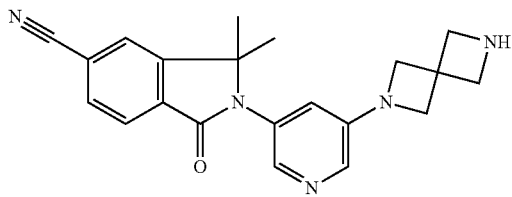 [SMILES: CC1(C)c2cc(C#N)ccc2C(=O)N1c1cncc(N2CC3(CNC3)C2)c1]

tert-Butyl-6-[5-(6-cyano-1,1-dimethyl-3-oxo-isoindolin-2-yl)-3-pyridyl]-2,6-diazaspiro[3.3]heptane-2-carboxylate (300 mg, 0.65 mmol) was treated with 30% TFA in DCM (12 mL) at room temperature for 15 min. The reaction solution was concentrated under reduced pressure to give the titled compound as oil, which was used directly in the next step without further purification. MS: 360.1 (M+H$^+$)

Intermediate B-5

6-[5-(2,6-Diazaspiro[3.3]heptan-2-yl)-3-pyridyl]-2-methoxy-7,7-dimethyl-pyrrolo[3,4-b]pyridin-5-one

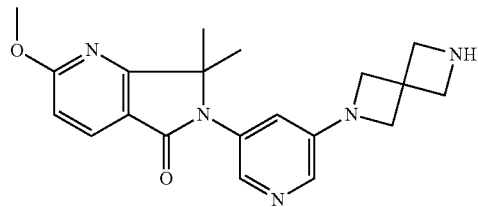 [SMILES: COc1ccc2c(n1)C(C)(C)N(c1cncc(N3CC4(CNC4)C3)c1)C2=O]

[A] 6-(5-Iodo-3-pyridyl)-2-methoxy-7,7-dimethyl-pyrrolo[3,4-b]pyridin-5-one

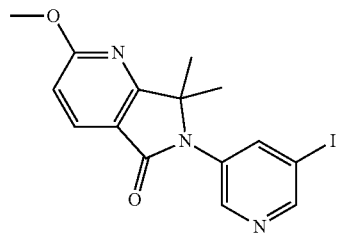 [SMILES: COc1ccc2c(n1)C(C)(C)N(c1cncc(I)c1)C2=O]

In a 75-mL sealed tube, 3,5-diiodopyridine (2.5 g, 7.5 mmol), 2-methoxy-7,7-dimethyl-6H-pyrrolo[3,4-b]pyridin-5-one (intermediate A-5, 576 mg, 3 mmol), CuI (345 mg, 1.8 mmol), K$_3$PO$_4$ (1.28 g, 6 mmol) and (+)-(S,S)-1,2-diamino-cyclohexane (0.12 mL, 1 mmol) were dissolved in dioxane (20 mL). The resulting reaction mixture was heated at 120° C. for 3 hours before it was poured into water (50 mL) and extracted with EtOAc (2×125 mL). The combined organic layers were washed with brine, dried over anhy. Na$_2$SO$_4$, filtered and concentrated in vacuo to give a crude product, which was purified by silica gel flash chromatography (0-60% EtOAc-hexane gradient) to afford the title compound (474 mg, 40.1%) as a light yellow solid. MS: 396.1 (M+H$^+$).

[B] tert-Butyl 6-[5-(2-methoxy-7,7-dimethyl-5-oxo-pyrrolo[3,4-b]pyridin-6-yl)-3-pyridyl]-2,6-diazaspiro[3.3]heptane-2-carboxylate

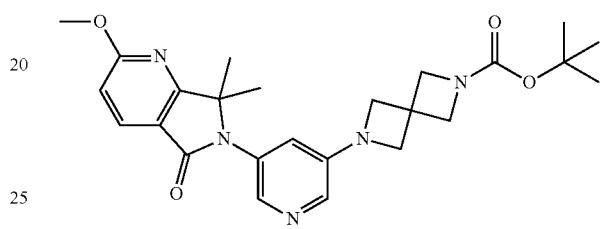

A mixture of 6-(5-iodo-3-pyridyl)-2-methoxy-7,7-dimethyl-pyrrolo[3,4-b]pyridin-5-one (395 mg, 1 mmol), tert-butyl 2,6-diazasprio[3.3]heptane-2-carboxylate oxalate (435 mg, 1.5 mmol), Pd$_2$(dba)$_3$ (70 mg), BINAP (85 mg), t-BuONa (290 mg, 3 mmol) and TEA (1 mL, 7.2 mmol) in toluene (20 mL) was stirred at 110° C. for 12 hours. After cooling to room temperature, the reaction mixture was poured into water (20 mL) and extracted with EtOAc (2×100 mL). The combined organic layers were washed with brine, dried over anhy. Na$_2$SO$_4$, filtered and concentrated in vacuo to give a crude product, which was purified by silica gel flash chromatography (30-100% EtOAc-hexane gradient) to afford the title compound (350 mg, 75.2%) as a light yellow foam. MS: 466.1 (M+H$^+$).

[C] 6-[5-(2,6-Diazaspiro[3.3]heptan-2-yl)-3-pyridyl]-2-methoxy-7,7-dimethyl-pyrrolo[3,4-b]pyridin-5-one

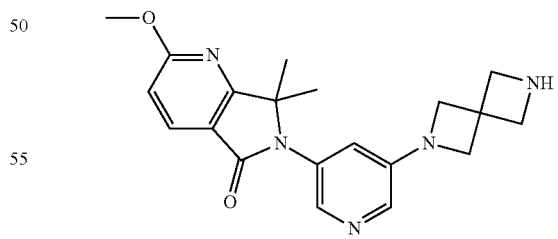

A solution of tert-butyl 6-[5-(2-methoxy-7,7-dimethyl-5-oxo-pyrrolo[3,4-b]pyridin-6-yl)-3-pyridyl]-2,6-diazaspiro[3.3]heptane-2-carboxylate (350 mg, 0.75 mmol) and TFA (2 mL) in DCM (5 mL) was stirred at room temperature for 2 hours. The resulting mixture was concentrated in vacuo to afford the crude title compound (450 mg) as light yellow oil, which was used directly in the next step without further purification. MS: 366.1 (M+H$^+$).

Intermediate B-6

5'-Chloro-2'-[5-(2,6-diazaspiro[3.3]heptan-2-yl)-3-pyridyl]spiro[cyclopropane-1,3'-isoindoline]-1'-one

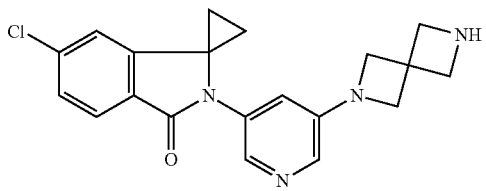 [SMILES: O=C1c2ccc(Cl)cc2C2(CC2)N1c1cncc(N2CC3(CNC3)C2)c1]

[A] 5'-Chloro-2'-(5-iodo-3-pyridyl)spiro[cyclopropane-1,3'-isoindoline]-1'-one

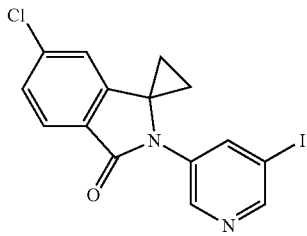 [SMILES: O=C1c2ccc(Cl)cc2C2(CC2)N1c1cncc(I)c1]

In a 75-mL sealed tube, 3,5-diiodopyridine (2.5 g, 7.5 mmol), 5'-chlorospiro[cyclopropane-1,3'-isoindoline]-1'-one (intermediate A-6, 579 mg, 3 mmol), CuI (345 mg, 1.8 mmol), K$_3$PO$_4$ (1.28 g, 6 mmol) and (+)-(S,S)-1,2-diaminocyclohexane (0.12 mL, 1 mmol) were dissolved in dioxane (20 mL). The resulting reaction mixture was heated at 120° C. for 3 hours before it was poured into water (50 mL) and extracted with EtOAc (2×125 mL). The combined organic layers were washed with brine, dried over anhy. Na$_2$SO$_4$, filtered and concentrated in vacuo to give a crude product, which was purified by silica gel flash chromatography (0-60% EtOAc-hexane gradient) to afford the title compound (436 mg, 36.7%) as a light yellow solid. MS: 397.1 (M+H$^+$).

[B] tert-Butyl 6-[5-(6'-chloro-3'-oxo-spiro[cyclopropane-1,1'-isoindoline]-2'-yl)-3-pyridyl]-2,6-diazaspiro[3.3]heptane-2-carboxylate

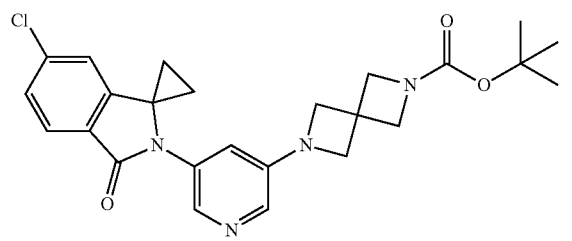 [SMILES: CC(C)(C)OC(=O)N1CC2(C1)CN(c1cncc(N3C(=O)c4ccc(Cl)cc4C34CC4)c1)C2]

A solution of 5'-chloro-2'-(5-iodo-3-pyridyl)spiro[cyclopropane-1,3'-isoindoline]-1'-one (396 mg, 1 mmol), tert-butyl 2,6-diazasprio[3.3]heptane-2-carboxylate oxalate (435 mg, 1.5 mmol), Pd$_2$(dba)$_3$ (70 mg), BINAP (85 mg), t-BuONa (290 mg, 3 mmol) and TEA (1 mL, 7.2 mmol) in toluene (20 mL) was stirred at 110° C. for 12 hours. After cooling to room temperature, the reaction mixture was poured into water (20 mL) and extracted with EtOAc (2×100 mL). The combined organic layers were washed with brine, dried over anhy. Na$_2$SO$_4$, filtered and concentrated in vacuo to give a crude product, which was purified by silica gel flash chromatography (30-100% EtOAc-hexane gradient) to afford the title compound (414 mg, 88.9%) as a light yellow foam. MS: 467.1 (M+H$^+$).

[C] 5'-Chloro-2'-[5-(2,6-diazaspiro[3.3]heptan-2-yl)-3-pyridyl]spiro[cyclopropane-1,3'-isoindoline]-1'-one

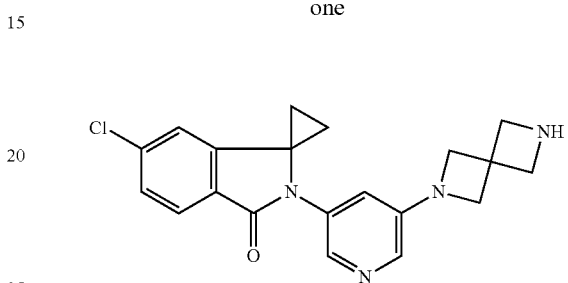

A solution of tert-butyl 6-[5-(6'-chloro-3'-oxo-spiro[cyclopropane-1,1'-isoindoline]-2'-yl)-3-pyridyl]-2,6-diazaspiro[3.3]heptane-2-carboxylate (414 mg, 0.889 mmol) and TFA (2 mL) in DCM (5 mL) was stirred at room temperature for 2 hours. The resulting mixture was concentrated in vacuo to afford the crude title compound (550 mg) as light yellow oil, which was used directly in the next step without further purification. MS: 367.1 (M+H$^+$).

Intermediate B-7

5-Chloro-2-[5-(2,6-diazaspiro[3.3]heptan-2-yl)-4-methyl-3-pyridyl]-3-methyl-isoindolin-1-one

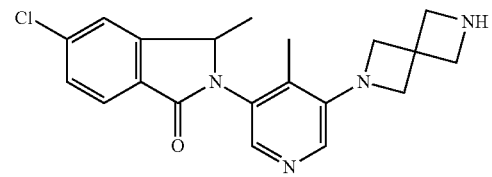 [SMILES: Cc1c(N2CC3(CNC3)C2)cncc1N1C(=O)c2ccc(Cl)cc2C1C]

[A] 3,5-Diiodo-4-methyl-pyridine

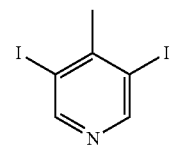

A solution of 3,5-dibromo-4-methyl-pyridine (10.0 g, 39.8 mmol), KI (70.0 g, 422 mmol), N,N'-dimethylethane-1,2-diamine (4.0 g, 45.4 mmol), CuI (4.0 g, 21.0 mmol) in dioxane (150 mL) was heated at 130° C. for 16 hours. After cooling to room temperature, the mixture was filtered and the filtrate was concentrated in vacuo to give the title compound (8.9 g, 65%) as a yellow solid. MS: 346.1 (M+H⁺).

[B] 5-Chloro-2-(5-iodo-4-methyl-3-pyridyl)-3-methyl-isoindolin-1-one

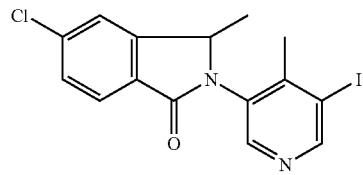 [SMILES: Cc1c(I)cncc1N1C(=O)c2ccc(Cl)cc2C1C]

A mixture of 3,5-diiodo-4-methyl-pyridine (3.45 g, 10.0 mmol), 5-chloro-3-methyl-isoindolin-1-one (intermediate A-2, 1.0 g, 5.5 mmol), trans-cyclohexane-1,2-diamine (500 mg, 4.3 mmol) and K₃PO₄ (2.7 g, 12.2 mmol) in dioxane (30 mL) was heated at 120° C. for 6 hours. After cooling to room temperature, the solvent was evaporated. The residue was purified by silica gel flash chromatography (PE:EtOAc=3:1) to afford the title compound (600 mg, 15%) as a yellow solid. MS: 399.3 (M+H⁺).

[C] tert-Butyl 6-[5-(5-chloro-3-methyl-1-oxo-isoindolin-2-yl)-4-methyl-3-pyridyl]-2,6-diazaspiro[3.3]heptane-2-carboxylate

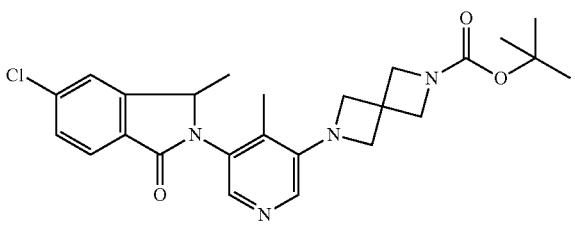 [SMILES: Cc1c(N2CC3(CN(C(=O)OC(C)(C)C)C3)C2)cncc1N1C(=O)c2ccc(Cl)cc2C1C]

A mixture of 5-chloro-2-(5-iodo-4-methyl-3-pyridyl)-3-methyl-isoindolin-1-one (300 mg, 0.75 mmol), tert-butyl 2,6-diazaspiro[3.3]heptane-2-carboxylate oxalate (300 mg, 1.04 mmol), Pd₂(dba)₃ (80 mg), BINAP (80 mg), tBuONa (240 mg, 2.5 mmol) and triethylamine (0.5 mL) in toluene (5 mL) was heated at 100° C. for 10 hours. After cooling to room temperature, the reaction mixture was diluted with satd. aq. NaCl solution (5 ml), extracted with EtOAc (4×10 mL), dried over anhy. Na₂SO₄, filtered, and concentrated under vacuum to give a crude product, which was purified by silica gel flash chromatography (PE:EtOAc=2:1) to afford the title compound (160 mg, 45%) as a yellow solid. MS: 369.1 (M+H⁺).

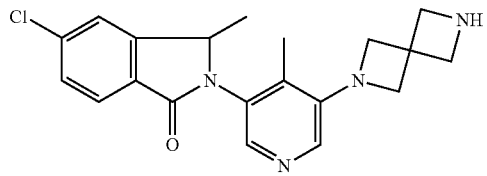 [SMILES: Cc1c(N2CC3(CNC3)C2)cncc1N1C(=O)c2ccc(Cl)cc2C1C]

[D] 5-Chloro-2-[5-(2,6-diazaspiro[3.3]heptan-2-yl)-4-methyl-3-pyridyl]-3-methyl-isoindolin-1-one A solution of tert-butyl 6-[5-(5-chloro-3-methyl-1-oxo-isoindolin-2-yl)-4-methyl-3-pyridyl]-2,6-diazaspiro[3.3] heptane-2-carboxylate (160 mg, 0.34 mmol) in DCM/TFA (4 mL/4 mL) was stirred at room temperature for 2 hours. The solvent was then evaporated to dryness and afford the title compound (300 mg, 100%) as brownish oil. MS: 469.1 (M+H⁺).

Intermediate B-8

5-Chloro-2-[5-(2,7-diazaspiro[3.5]nonan-2-yl)-3-pyridyl]-3,3-dimethyl-isoindolin-1-one

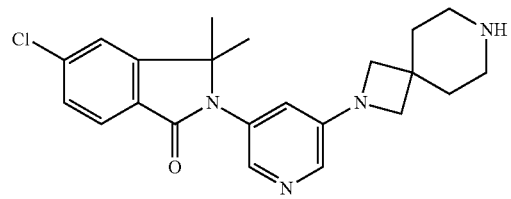 [SMILES: CC1(C)c2cc(Cl)ccc2C(=O)N1c1cncc(N2CC3(CCNCC3)C2)c1]

[A] 2-(5-Bromo-3-pyridyl)-5-chloro-3,3-dimethyl-isoindolin-1-one

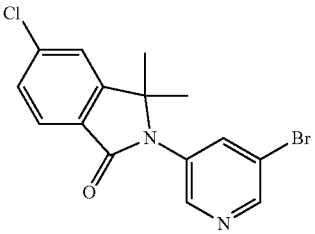 [SMILES: CC1(C)c2cc(Cl)ccc2C(=O)N1c1cncc(Br)c1]

In a 75-mL sealed tube, 3-bromo-5-iodo-pyridine (4.3 g, 15 mmol), 5-chloro-3,3-dimethyl-isoindolin-1-one (intermediate A-3, 1.95 g, 10 mmol), CuI (1.4 g, 6 mmol), K₃PO₄ (4.24 g, 20 mmol) and (+)-(S,S)-1,2-diaminocyclohexane (0.7 mL, 6 mmol) were dissolved in dioxane (20 mL). The resulting reaction mixture was heated at 120° C. for 3 hours before it was poured into water (50 mL) and extracted with EtOAc (2×125 mL). The combined organic layers were washed with brine, dried over anhy. Na₂SO₄, filtered and concentrated in vacuo to give a crude product, which was purified by silica gel flash chromatography (0-60% EtOAc-hexane gradient) to yield the title compound (2.5 g, 71.2%) as a light yellow solid. MS: 351.1 & 353.1 (M+H⁺).

[B] tert-Butyl 2-[5-(6-chloro-1,1-dimethyl-3-oxo-isoindolin-2-yl)-3-pyridyl]-2,7-diazaspiro[3.5]nonane-7-carboxylate

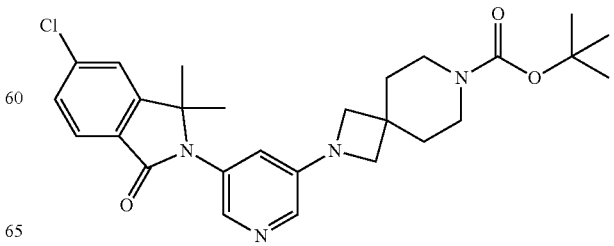

A solution of 2-(5-bromo-3-pyridyl)-5-chloro-3,3-dimethyl-isoindolin-1-one (351 mg, 1 mmol), tert-butyl 2,7-diazaspiro[3.5]nonane-7-carboxylate (400 mg, 1.7 mmol), Pd$_2$(dba)$_3$ (70 mg), BINAP (85 mg), t-BuONa (400 mg, 4 mmol) and TEA (0.5 mL, 4 mmol) in toluene (10 mL) was stirred at 110° C. for 12 hours. After cooling to room temperature, the reaction mixture was poured into water (20 mL) and extracted with EtOAc (2×100 mL). The combined organics were washed with brine, dried over anhy. Na$_2$SO$_4$, filtered and concentrated in vacuo to give a crude product, which was purified by silica gel flash chromatography (30-100% EtOAc-hexane gradient) to yield the title compound (370 mg, 74.6%) as light yellow oil. MS: 497.1 (M+H$^+$).

[C] 5-Chloro-2-[5-(2,7-diazaspiro[3.5]nonan-2-yl)-3-pyridyl]-3,3-dimethyl-isoindolin-1-one

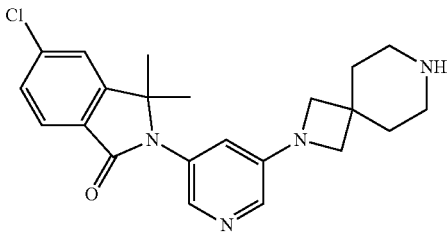 [SMILES: CC1(C)c2cc(Cl)ccc2C(=O)N1c1cncc(N2CC3(CCNCC3)C2)c1]

A solution of tert-butyl 2-[5-(6-chloro-1,1-dimethyl-3-oxo-isoindolin-2-yl)-3-pyridyl]-2,7-diazaspiro[3.5]nonane-7-carboxylate (370 mg, 0.746 mmol) and TFA (1 mL) in DCM (3 mL) was stirred at room temperature for 2 hours. The resulting mixture solution was concentrated in vacuo to give a crude product (400 mg) as light yellow oil, which was used directly in the next step without further purification. MS: 397.1 (M+H$^+$).

Intermediate B-9

5-Chloro-2-[5-(2,7-diazaspiro[3.5]nonan-7-yl)-3-pyridyl]-3,3-dimethyl-isoindolin-1-one

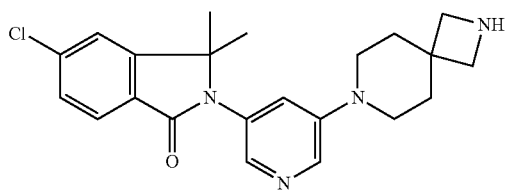 [SMILES: CC1(C)c2cc(Cl)ccc2C(=O)N1c1cncc(N2CCC3(CC2)CNC3)c1]

[A] tert-Butyl 7-[5-(6-chloro-1,1-dimethyl-3-oxo-isoindolin-2-yl)-3-pyridyl]-2,7-diazaspiro[3.5]nonane-2-carboxylate

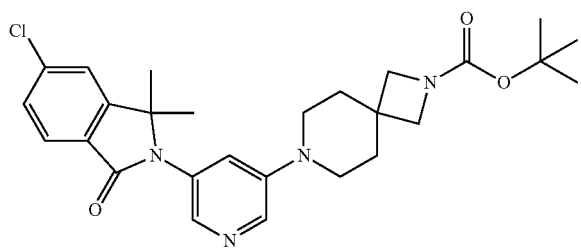 [SMILES: CC(C)(C)OC(=O)N1CC2(CCN(c3cncc(N4C(=O)c5ccc(Cl)cc5C4(C)C)c3)CC2)C1]

A solution of 2-(5-bromo-3-pyridyl)-5-chloro-3,3-dimethyl-isoindolin-1-one (351 mg, 1 mmol, Intermediate B-8 [A]), tert-butyl 2,7-diazaspiro[3.5]nonane-2-carboxylate (400 mg, 1.7 mmol), Pd$_2$(dba)$_3$ (70 mg), BINAP (85 mg), t-BuONa (400 mg, 4 mmol) and TEA (0.5 mL, 4 mmol) in toluene (10 mL) was stirred at 11° C. for 12 hours. After cooling to room temperature, the reaction mixture was poured into water (20 mL) and extracted with EtOAc (2×100 mL). The combined organic layers were washed with brine, dried over anhy. Na$_2$SO$_4$, filtered and concentrated in vacuo to give a crude product, which was purified by silica gel flash chromatography (30-100% EtOAc-hexane gradient) to yield the title compound (330 mg, 66.6%) as light yellow oil. MS: 497.1 (M+H$^+$).

[B] 5-Chloro-2-[5-(2,7-diazaspiro[3.5]nonan-7-yl)-3-pyridyl]-3,3-dimethyl-isoindolin-1-one

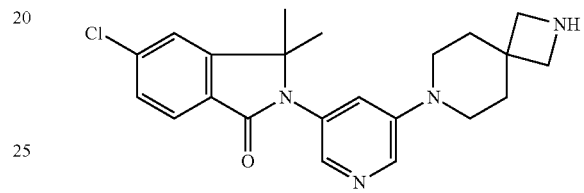

A solution of tert-butyl 7-[5-(6-chloro-1,1-dimethyl-3-oxo-isoindolin-2-yl)-3-pyridyl]-2,7-diazaspiro[3.5]nonane-2-carboxylate (330 mg, 0.666 mmol) and TFA (1 mL) in DCM (3 mL) was stirred at room temperature for 2 hours. The resulting mixture was concentrated in vacuo to give a crude product (400 mg) as light yellow oil, which was used in the next step without further purification. MS: 397.1 (M+H$^+$).

Example 1

5-Chloro-3,3-dimethyl-2-[5-[2-(1-methylpyrazole-4-carbonyl)-2,6-diazaspiro[3.3]-heptan-6-yl]-3-pyridyl]isoindolin-1-one

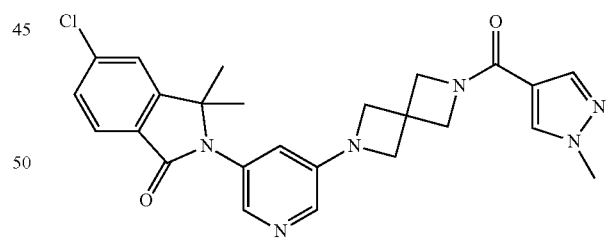

To a solution of 5-chloro-2-[5-(2,6-diazaspiro[3.3]heptan-2-yl)-3-pyridyl]-3,3-dimethyl-isoindolin-1-one (intermediate B-3, 1.6 g, 3.2 mmol) and 1-methylpyrazole-4-carboxylic acid (1.1 g, 8.7 mmol) in DCM was added BOP-Cl (3.7 g, 8.4 mmol) and DIEPA (2.0 g, 15.5 mmol) at 0° C. The reaction mixture was allowed to warm up to room temperature and stirred overnight. Brine was added to quench the reaction and the mixture was extracted with DCM twice. The organic layers were combined, washed with brine, dried over anhy. Na$_2$SO$_4$, filtered and concentrated in vacuo to give a yellow oily residue, which was purified by silica gel flash chromatography to afford the title compound (680 mg, 45%) as a white foam. MS: 477.3 (M+H$^+$).

The following examples listed in Table 1 were prepared in analogy to the procedure described for the preparation of example 1. And whenever necessary, chiral separation was used to afford the respective chiral compounds.

TABLE 1

| Example | Name<br>Structure<br>Aspect | Reactants | MS<br>(M + H⁺) |
|---|---|---|---|
| 2 | 5-Chloro-2-[5-[2-(1-ethylpyrazole-4-carbonyl)-2,6-diazaspiro[3.3]-heptan-6-yl]-3-pyridyl]-3,3-dimethyl-isoindolin-1-one<br>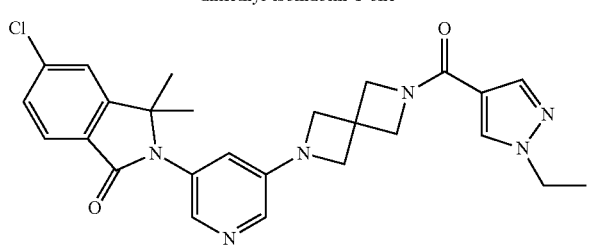<br>White foam | 5-Chloro-2-[5-(2,6-diazaspiro[3.3]heptan-2-yl)-3-pyridyl]-3,3-dimethyl-isoindolin-1-one (intermediate B-3) and 1-ethylpyrazole-4-carboxylic acid | 491.1 |
| 3 | 5-Chloro-2-[5-[2-(1-isopropylpyrazole-4-carbonyl)-2,6-diazaspiro[3.3]-heptan-6-yl]-3-pyridyl]-3,3-dimethyl-isoindolin-1-one<br>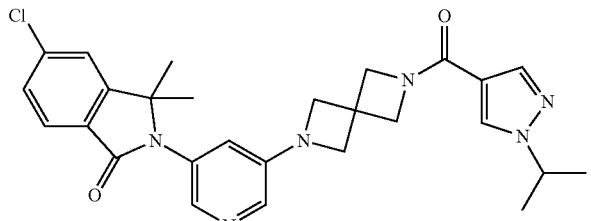<br>White foam | 5-Chloro-2-[5-(2,6-diazaspiro[3.3]heptan-2-yl)-3-pyridyl]-3,3-dimethyl-isoindolin-1-one (intermediate B-3) and 1-isopropylpyrazole-4-carboxylic acid | 505.1 |
| 4 | 5-Chloro-3,3-dimethyl-2-[5-[2-(1-methylimidazole-2-carbonyl)-2,6-diazaspiro[3.3]-heptan-6-yl]-3-pyridyl]-isoindolin-1-one<br>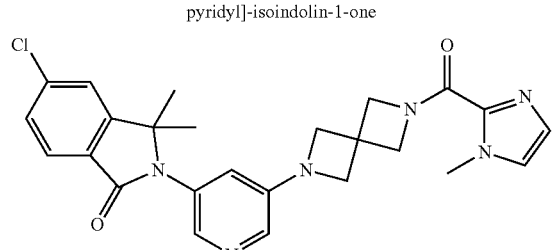<br>White foam | 5-Chloro-2-[5-(2,6-diazaspiro[3.3]heptan-2-yl)-3-pyridyl]-3,3-dimethyl-isoindolin-1-one (intermediate B-3) and 1-methylimidazole-2-carboxylic acid | 477.1 |

TABLE 1-continued

| Example | Name Structure Aspect | Reactants | MS (M + H⁺) |
|---|---|---|---|
| 5 | 5-Chloro-3,3-dimethyl-2-[5-[2-(2-methylpyrazole-3-carbonyl)-2,6-diazaspiro[3.3]heptan-6-yl]-3-pyridyl]-isoindolin-1-one<br />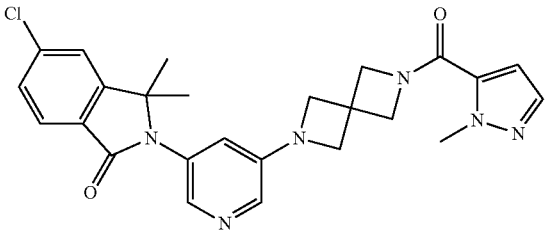<br />White foam | 5-Chloro-2-[5-(2,6-diazaspiro[3.3]heptan-2-yl)-3-pyridyl]-3,3-dimethyl-isoindolin-1-one (intermediate B-3) and 2-methylpyrazole-3-carboxylic acid | 477.1 |
| 6 | 5-Chloro-3,3-dimethyl-2-[5-[2-(3-methylimidazole-4-carbonyl)-2,6-diazaspiro[3.3]heptan-6-yl]-3-pyridyl]-isoindolin-1-one<br />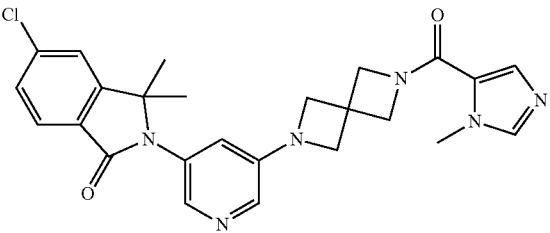<br />White foam | 5-Chloro-2-[5-(2,6-diazaspiro[3.3]heptan-2-yl)-3-pyridyl]-3,3-dimethyl-isoindolin-1-one (intermediate B-3) and 3-methylimidazole-4-carboxylic acid | 477.1 |
| 7 | 5-Chloro-3,3-dimethyl-2-[5-[2-(4-methylpyridine-3-carbonyl)-2,6-diazaspiro[3.3]heptan-6-yl]-3-pyridyl]-isoindolin-1-one<br />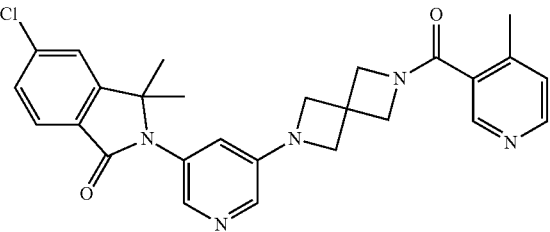<br />White foam | 5-Chloro-2-[5-(2,6-diazaspiro[3.3]heptan-2-yl)-3-pyridyl]-3,3-dimethyl-isoindolin-1-one (intermediate B-3) and 4-methylpyridine-3-carboxylic acid | 488.2 |
| 8 | 3,3-Dimethyl-2-[5-[2-(1-methylpyrazole-4-carbonyl)-2,6-diazaspiro[3.3]heptan-6-yl]-3-pyridyl]-1-oxo-isoindoline-5-carbonitrile<br />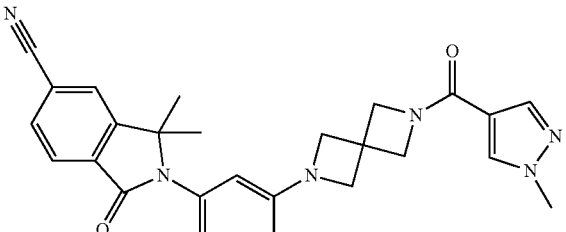<br />White foam | 2-[5-(2,6-Diazaspiro[3.3]heptan-2-yl)-3-pyridyl]-3,3-dimethyl-1-oxo-isoindoline-5-carbonitrile (intermediate B-4) and 1-methylpyrazole-4-carboxylic acid | 468.2 |

TABLE 1-continued

| Example | Name Structure Aspect | Reactants | MS (M + H+) |
|---|---|---|---|
| 9 | 2-[5-[2-(1-Ethylpyrazole-4-carbonyl)-2,6-diazaspiro[3.3]heptan-6-yl]-3-pyridyl]-3,3-dimethyl-1-oxo-isoindoline-5-carbonitrile<br>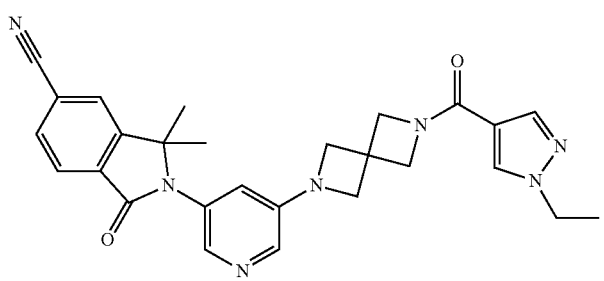<br>White foam | 2-[5-(2,6-Diazaspiro[3.3]heptan-2-yl)-3-pyridyl]-3,3-dimethyl-1-oxo-isoindoline-5-carbonitrile (intermediate B-4) and 1-ethylpyrazole-4-carboxylic acid | 482.1 |
| 10 | 2-[5-[2-(1-Isopropylpyrazole-4-carbonyl)-2,6-diazaspiro[3.3]heptan-6-yl]-3-pyridyl]-3,3-dimethyl-1-oxo-isoindoline-5-carbonitrile<br>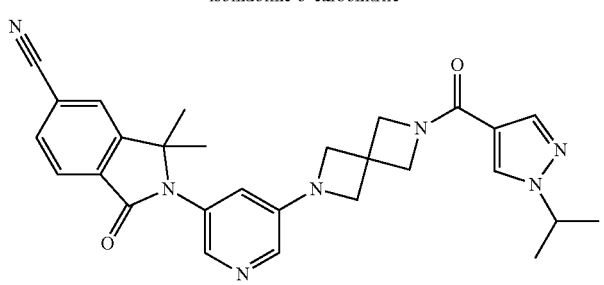<br>White foam | 2-[5-(2,6-Diazaspiro[3.3]heptan-2-yl)-3-pyridyl]-3,3-dimethyl-1-oxo-isoindoline-5-carbonitrile (intermediate B-4) and 1-isopropylpyrazole-4-carboxylic acid | 496.2 |
| 11 | 3,3-Dimethyl-2-[5-[2-(1-methylimidazole-2-carbonyl)-2,6-diazaspiro[3.3]heptan-6-yl]-3-pyridyl]-1-oxo-isoindoline-5-carbonitrile<br>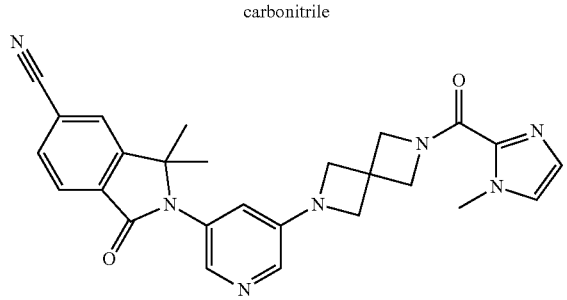<br>White foam | 2-[5-(2,6-Diazaspiro[3.3]heptan-2-yl)-3-pyridyl]-3,3-dimethyl-1-oxo-isoindoline-5-carbonitrile (intermediate B-4) and 1-methylimidazole-2-carboxylic acid | 468.2 |

TABLE 1-continued

| Example | Name / Structure / Aspect | Reactants | MS (M + H+) |
|---|---|---|---|
| 12 | 3,3-Dimethyl-2-[5-[2-(2-methylpyrazole-3-carbonyl)-2,6-diazaspiro[3.3]heptan-6-yl]-3-pyridyl]-1-oxo-isoindoline-5-carbonitrile<br>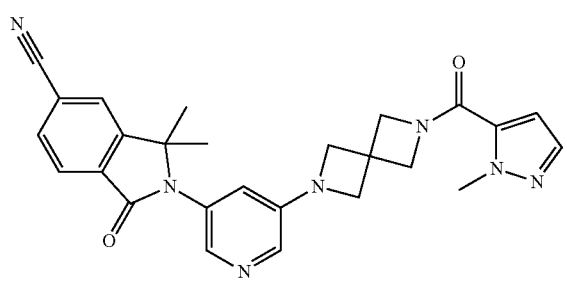<br>White foam | 2-[5-(2,6-Diazaspiro[3.3]heptan-2-yl)-3-pyridyl]-3,3-dimethyl-1-oxo-isoindoline-5-carbonitrile (intermediate B-4) and 2-methylpyrazole-3-carboxylic acid | 468.2 |
| 13 | 3,3-Dimethyl-2-[5-[2-(3-methylimidazole-4-carbonyl)-2,6-diazaspiro[3.3]heptan-6-yl]-3-pyridyl]-1-oxo-isoindoline-5-carbonitrile<br>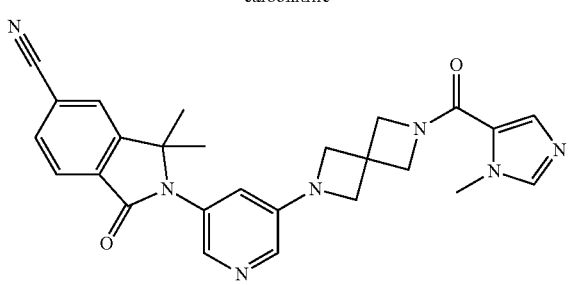<br>White foam | 2-[5-(2,6-Diazaspiro[3.3]heptan-2-yl)-3-pyridyl]-3,3-dimethyl-1-oxo-isoindoline-5-carbonitrile (intermediate B-4) and 3-methylimidazole-4-carboxylic acid | 468.2 |
| 14 | 3,3-Dimethyl-2-[5-[2-(4-methylpyridine-3-carbonyl)-2,6-diazaspiro[3.3]heptan-6-yl]-3-pyridyl]-1-oxo-isoindoline-5-carbonitrile<br>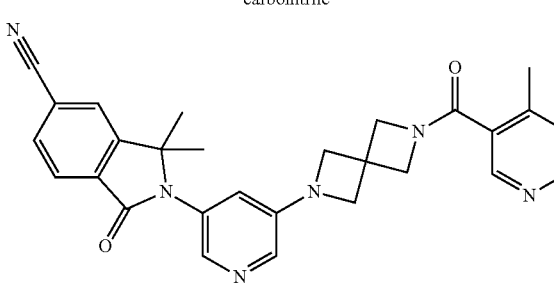<br>White foam | 2-[5-(2,6-Diazaspiro[3.3]heptan-2-yl)-3-pyridyl]-3,3-dimethyl-1-oxo-isoindoline-5-carbonitrile (intermediate B-4) and 4-methylpyridine-3-carboxylic acid | 479.1 |

TABLE 1-continued

| Example | Name Structure Aspect | Reactants | MS (M + H+) |
|---|---|---|---|
| 15 | 2-Methoxy-7,7-dimethyl-6-[5-[2-(1-methylpyrazole-4-carbonyl)-2,6-diazaspiro[3.3]heptan-6-yl]-3-pyridyl]pyrrolo[3,4-b]pyridin-5-one<br>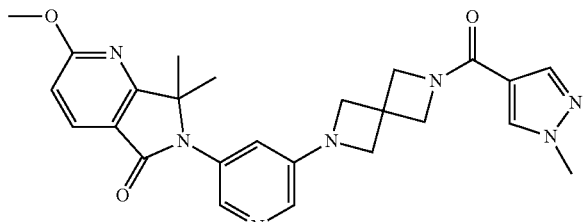<br>White foam | 6-[5-(2,6-Diazaspiro[3.3]heptan-2-yl)-3-pyridyl]-2-methoxy-7,7-dimethyl-pyrrolo[3,4-b]pyridin-5-one (intermediate B-5) and 1-methylpyrazole-4-carboxylic acid | 474.1 |
| 16 | 2-Methoxy-7,7-dimethyl-6-[5-[2-(4-methylpyridine-3-carbonyl)-2,6-diazaspiro[3.3]heptan-6-yl]-3-pyridyl]pyrrolo[3,4-b]pyridin-5-one<br>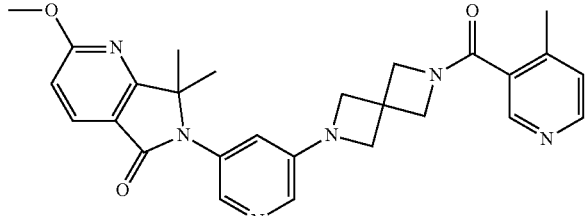<br>White foam | 6-[5-(2,6-Diazaspiro[3.3]heptan-2-yl)-3-pyridyl]-2-methoxy-7,7-dimethyl-pyrrolo[3,4-b]pyridin-5-one (intermediate B-5) and 4-methylpyridine-3-carboxylic acid | 485.1 |
| 17 | 2-Methoxy-7,7-dimethyl-6-[5-[2-(2-methylpyrazole-3-carbonyl)-2,6-diazaspiro[3.3]heptan-6-yl]-3-pyridyl]pyrrolo[3,4-b]pyridin-5-one<br>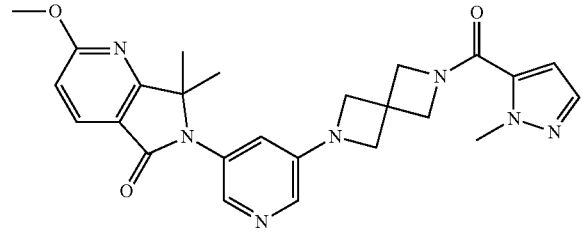<br>White foam | 6-[5-(2,6-Diazaspiro[3.3]heptan-2-yl)-3-pyridyl]-2-methoxy-7,7-dimethyl-pyrrolo[3,4-b]pyridin-5-one (intermediate B-5) and 2-methylpyrazole-3-carboxylic acid | 474.1 |
| 18 | 5-Chloro-3-methyl-2-[5-[2-(1-methylpyrazole-4-carbonyl)-2,6-diazaspiro[3.3]heptan-6-yl]-3-pyridyl]isoindolin-1-one<br>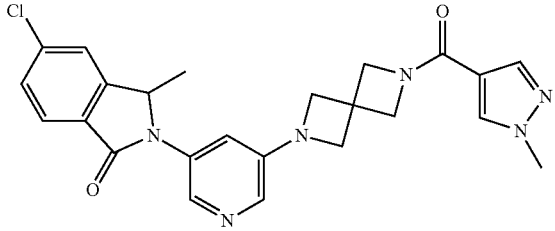<br>White foam | 5-Chloro-2-[5-(2,6-diazaspiro[3.3]heptan-2-yl)-3-pyridyl]-3-methyl-isoindolin-1-one (intermediate B-2) and 1-methylpyrazole-4-carboxylic acid | 463.1 |

TABLE 1-continued

| Example | Name Structure Aspect | Reactants | MS (M + H+) |
|---|---|---|---|
| 19 | 5'-Chloro-2'-[5-[2-(1-methylpyrazole-4-carbonyl)-2,6-diazaspiro[3.3]heptan-6-yl]-3-pyridyl]spiro[cyclopropane-1,3'-isoindoline]-1'-one<br />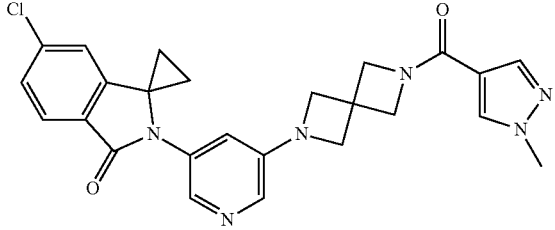<br />White foam | 5'-Chloro-2'-[5-(2,6-diazaspiro[3.3]heptan-2-yl)-3-pyridyl]spiro[cyclopropane-1,3'-isoindoline]-1'-one (intermediate B-6) and 1-methylpyrazole-4-carboxylic acid | 475.1 |
| 20 | 5'-Chloro-2'-[5-[2-(4-methylpyridine-3-carbonyl)-2,6-diazaspiro[3.3]heptan-6-yl]-3-pyridyl]spiro[cyclopropane-1,3'-isoindoline]-1'-one<br />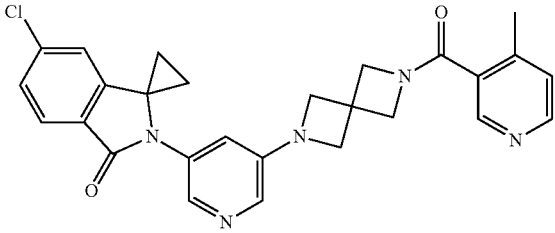<br />White foam | 5'-Chloro-2'-[5-(2,6-diazaspiro[3.3]heptan-2-yl)-3-pyridyl]spiro[cyclopropane-1,3'-isoindoline]-1'-one (intermediate B-6) and 4-methylpyridine-3-carboxylic acid | 486.1 |
| 21 | 5'-Chloro-2'-[5-[2-(2-methylpyrazole-4-carbonyl)-2,6-diazaspiro[3.3]heptan-6-yl]-3-pyridyl]spiro[cyclopropane-1,3'-isoindoline]-1'-one<br />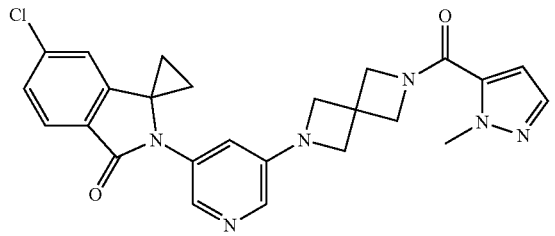<br />White foam | 5'-Chloro-2'-[5-(2,6-diazaspiro[3.3]heptan-2-yl)-3-pyridyl]spiro[cyclopropane-1,3'-isoindoline]-1'-one (intermediate B-6) and 2-methylpyrazole-3-carboxylic acid | 475.1 |

TABLE 1-continued

| Example | Name Structure Aspect | Reactants | MS (M + H+) |
|---|---|---|---|
| 22 | (3R or 3S)-5-Chloro-3-methyl-2-[5-[2-(1-methylpyrazole-4-carbonyl)-2,6-diazaspiro[3.3]heptan-6-yl]-3-pyridyl]isoindolin-1-one<br>Chiral<br>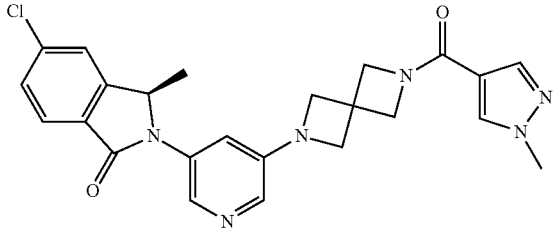<br>White foam | 5-Chloro-2-[5-(2,6-diazaspiro[3.3]heptan-2-yl)-3-pyridyl]-3-methyl-isoindolin-1-one (intermediate B-2) and 1-methylpyrazole-4-carboxylic acid<br>Chiral separation | 463.1 |
| 23 | (3S or 3R)-5-Chloro-3-methyl-2-[5-[2-(1-methylpyrazole-4-carbonyl)-2,6-diazaspiro[3.3]heptan-6-yl]-3-pyridyl]isoindolin-1-one<br>Chiral<br>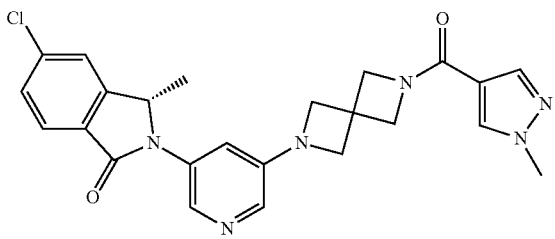<br>White foam | 5-Chloro-2-[5-(2,6-diazaspiro[3.3]heptan-2-yl)-3-pyridyl]-3-methyl-isoindolin-1-one (intermediate B-2) and 1-methylpyrazole-4-carboxylic acid<br>Chiral separation | 463.1 |
| 24 | 5-Chloro-2-[5-[2-(4-methylpyridine-3-carbonyl)-2,6-diazaspiro[3.3]heptan-6-yl]-3-pyridyl]-3,3-dimethyl-isoindolin-1-one<br>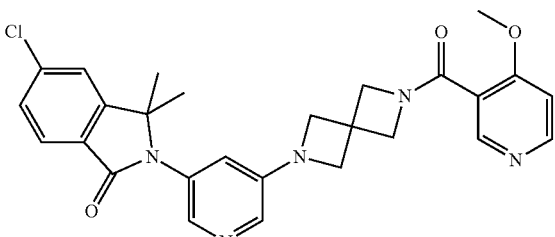<br>White foam | 5-Chloro-2-[5-(2,6-diazaspiro[3.3]heptan-2-yl)-3-pyridyl]-3,3-dimethyl-isoindolin-1-one (intermediate B-3) and 4-methoxypyridine-3-carboxylic acid | 504.1 |

TABLE 1-continued

| Example | Name Structure Aspect | Reactants | MS (M + H+) |
|---|---|---|---|
| 25 | 5-Chloro-2-[5-[2-(3,6-dimethylpyrazine-2-carbonyl)-2,6-diazaspiro[3.3]heptan-6-yl]-3-pyridyl]-3,3-dimethyl-isoindolin-1-one<br><br>White foam | 5-Chloro-2-[5-(2,6-diazaspiro[3.3]heptan-2-yl)-3-pyridyl]-3,3-dimethyl-isoindolin-1-one (intermediate B-3) and 3,6-dimethylpyrazine-2-carboxylic acid | 502.1 |
| 26 | 5-Chloro-2-[5-[2-(1,5-dimethylpyrazole-4-carbonyl)-2,6-diazaspiro[3.3]heptan-6-yl]-3-pyridyl]-3,3-dimethyl-isoindolin-1-one<br><br>White foam | 5-Chloro-2-[5-(2,6-diazaspiro[3.3]heptan-2-yl)-3-pyridyl]-3,3-dimethyl-isoindolin-1-one (intermediate B-3) and 1,5-dimethylpyrazole-4-carboxylic acid | 491.1 |
| 27 | 5-Chloro-3,3-dimethyl-2-[5-[2-(3-methylisoxazole-4-carbonyl)-2,6-diazaspiro[3.3]heptan-6-yl]-3-pyridyl]isoindolin-1-one<br><br>White foam | 5-Chloro-2-[5-(2,6-diazaspiro[3.3]heptan-2-yl)-3-pyridyl]-3,3-dimethyl-isoindolin-1-one (intermediate B-3) and 3-methylisoxazole-4-carboxylic acid | 478.1 |
| 28 | 5-Chloro-3,3-dimethyl-2-[5-[2-(6-methylpyrazine-2-carbonyl)-2,6-diazaspiro[3.3]heptan-6-yl]-3-pyridyl]isoindolin-1-one<br><br>White foam | 5-Chloro-2-[5-(2,6-diazaspiro[3.3]heptan-2-yl)-3-pyridyl]-3,3-dimethyl-isoindolin-1-one (intermediate B-3) and 6-methylpyrazine-2-carboxylic acid | 489.1 |

TABLE 1-continued

| Example | Name Structure Aspect | Reactants | MS (M + H+) |
|---|---|---|---|
| 29 | 5-Chloro-3,3-dimethyl-2-[5-[2-(4-methylpyrimidine-5-carbonyl)-2,6-diazaspiro[3.3]heptan-6-yl]-3-pyridyl]isoindolin-1-one<br>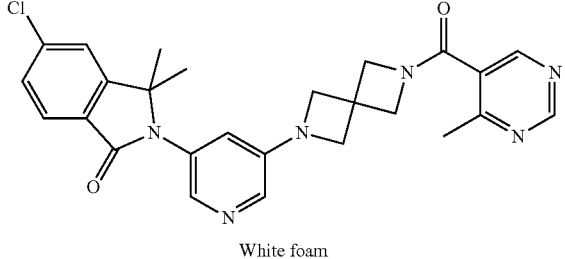<br>White foam | 5-Chloro-2-[5-(2,6-diazaspiro[3.3]heptan-2-yl)-3-pyridyl]-3,3-dimethyl-isoindolin-1-one (intermediate B-3) and 4-methylpyrimidine-5-carboxylic acid | 489.1 |
| 30 | 5-Chloro-3,3-dimethyl-2-[5-[2-(5-methylpyrazine-2-carbonyl)-2,6-diazaspiro[3.3]heptan-6-yl]-3-pyridyl]isoindolin-1-one<br>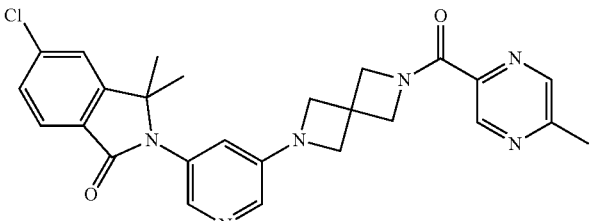<br>White foam | 5-Chloro-2-[5-(2,6-diazaspiro[3.3]heptan-2-yl)-3-pyridyl]-3,3-dimethyl-isoindolin-1-one (intermediate B-3) and 5-methylpyrazine-2-carboxylic acid | 489.1 |
| 31 | 5-Chloro-2-[5-[2-(2,5-dimethylpyrazole-3-carbonyl)-2,6-diazaspiro[3.3]heptan-6-yl]-3-pyridyl]-3,3-dimethyl-isoindolin-1-one<br>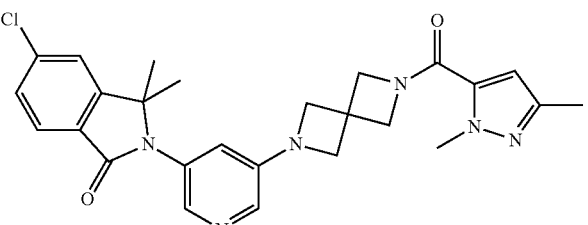<br>White foam | 5-Chloro-2-[5-(2,6-diazaspiro[3.3]heptan-2-yl)-3-pyridyl]-3,3-dimethyl-isoindolin-1-one (intermediate B-3) and 2,5-dimethylpyrazole-3-carboxylic acid | 491.1 |
| 32 | 5-Chloro-3,3-dimethyl-2-[5-[2-(5-methyloxazole-4-carbonyl)-2,6-diazaspiro[3.3]heptan-6-yl]-3-pyridyl]isoindolin-1-one<br>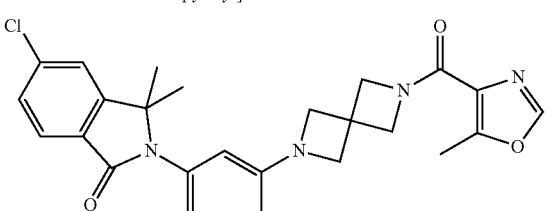<br>White foam | 5-Chloro-2-[5-(2,6-diazaspiro[3.3]heptan-2-yl)-3-pyridyl]-3,3-dimethyl-isoindolin-1-one (intermediate B-3) and 5-methyloxazole-4-carboxylic acid | 478.1 |

TABLE 1-continued

| Example | Name Structure Aspect | Reactants | MS (M + H⁺) |
|---|---|---|---|
| 33 | 5-Chloro-3,3-dimethyl-2-[5-[2-(pyrimidine-2-carbonyl)-2,6-diazaspiro[3.3]heptan-6-yl]-3-pyridyl]isoindolin-1-one<br />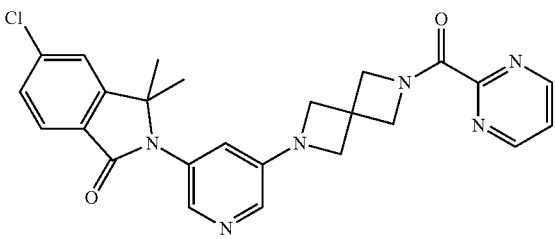<br />White foam | 5-Chloro-2-[5-(2,6-diazaspiro[3.3]heptan-2-yl)-3-pyridyl]-3,3-dimethyl-isoindolin-1-one (intermediate B-3) and pyrimidine-2-carboxylic acid | 475.1 |
| 34 | 5-Chloro-3,3-dimethyl-2-[5-[2-(5-methylpyrimidine-2-carbonyl)-2,6-diazaspiro[3.3]heptan-6-yl]-3-pyridyl]isoindolin-1-one<br />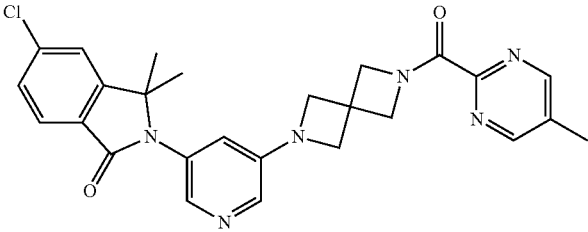<br />White foam | 5-Chloro-2-[5-(2,6-diazaspiro[3.3]heptan-2-yl)-3-pyridyl]-3,3-dimethyl-isoindolin-1-one (intermediate B-3) and 5-methylpyrimidine-2-carboxylic acid | 489.1 |
| 35 | 5-Chloro-2-[5-[2-[3-(difluoromethyl)-1-methyl-pyrazole-4-carbonyl]-2,6-diazaspiro[3.3]heptan-6-yl]-3-pyridyl]-3,3-dimethyl-isoindolin-1-one<br />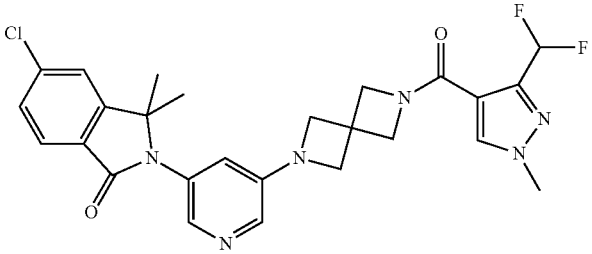<br />White foam | 5-Chloro-2-[5-(2,6-diazaspiro[3.3]heptan-2-yl)-3-pyridyl]-3,3-dimethyl-isoindolin-1-one (intermediate B-3) and 3-(difluoromethyl)-1-methyl-pyrazole-4-carboxylic acid | 527.1 |
| 36 | 5-[6-[5-(6-Chloro-1,1-dimethyl-3-oxo-isoindolin-2-yl)-3-pyridyl]-2,6-diazaspiro[3.3]heptane-2-carbonyl]pyridine-3-carbonitrile<br />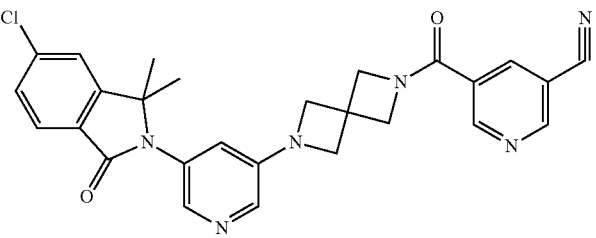<br />White foam | 5-Chloro-2-[5-(2,6-diazaspiro[3.3]heptan-2-yl)-3-pyridyl]-3,3-dimethyl-isoindolin-1-one (intermediate B-3) and 5-cyanopyridine-3-carboxylic acid | 499.1 |

| Example | Name Structure Aspect | Reactants | MS (M + H+) |
|---|---|---|---|
| 37 | 5-Chloro-2-[5-[2-(3-methoxypyrazine-2-carbonyl)-2,6-diazaspiro[3.3]heptan-6-yl]-3-pyridyl]-3,3-dimethyl-isoindolin-1-one<br />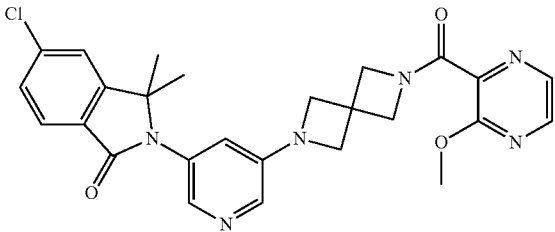<br />White foam | 5-Chloro-2-[5-(2,6-diazaspiro[3.3]heptan-2-yl)-3-pyridyl]-3,3-dimethyl-isoindolin-1-one (intermediate B-3) and 3-methoxypyrazine-2-carboxylic acid | 505.1 |
| 38 | 5-Chloro-3,3-dimethyl-2-[5-[2-(pyrazine-2-carbonyl)-2,6-diazaspiro[3.3]heptan-6-yl]-3-pyridyl]-isoindolin-1-one<br />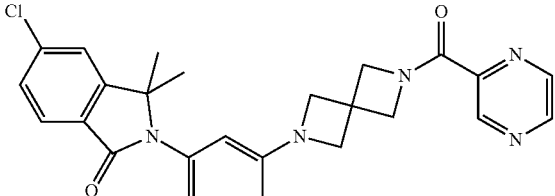<br />White foam | 5-Chloro-2-[5-(2,6-diazaspiro[3.3]heptan-2-yl)-3-pyridyl]-3,3-dimethyl-isoindolin-1-one (intermediate B-3) and pyrazine-2-carboxylic acid | 475.1 |
| 39 | 5-Chloro-3,3-dimethyl-2-[5-[2-(5-methylisoxazole-4-carbonyl)-2,6-diazaspiro[3.3]heptan-6-yl]-3-pyridyl]isoindolin-1-one<br />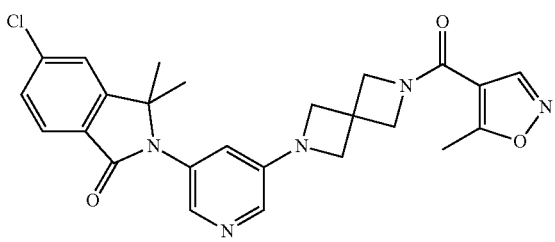 [SMILES: Cn1cc(C(=O)N2CC3(C2)CN(c2cncc(N4C(=O)c5ccc(Cl)cc5C4(C)C)c2)C3)cn1]<br />White foam | 5-Chloro-2-[5-(2,6-diazaspiro[3.3]heptan-2-yl)-3-pyridyl]-3,3-dimethyl-isoindolin-1-one (intermediate B-3) and 5-methylisoxazole-4-carboxylic acid | 478.1 |
| 40 | 5-Chloro-3,3-dimethyl-2-[5-[2-(pyrimidine-5-carbonyl)-2,6-diazaspiro[3.3]heptan-6-yl]-3-pyridyl]isoindolin-1-one<br />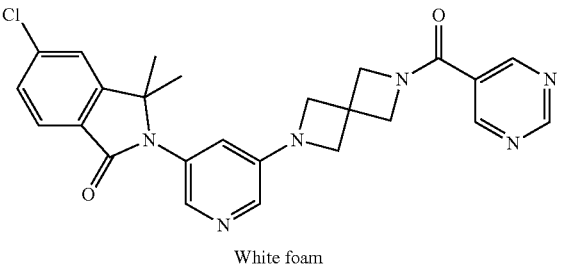<br />White foam | 5-Chloro-2-[5-(2,6-diazaspiro[3.3]heptan-2-yl)-3-pyridyl]-3,3-dimethyl-isoindolin-1-one (intermediate B-3) and pyrimidine-5-carboxylic acid | 475.1 |

TABLE 1-continued

| Example | Name Structure Aspect | Reactants | MS (M + H⁺) |
|---|---|---|---|
| 41 | 5-Chloro-3,3-dimethyl-2-[5-[2-(4-methyloxazole-5-carbonyl)-2,6-diazaspiro[3.3]heptan-6-yl]-3-pyridyl]isoindolin-1-one<br />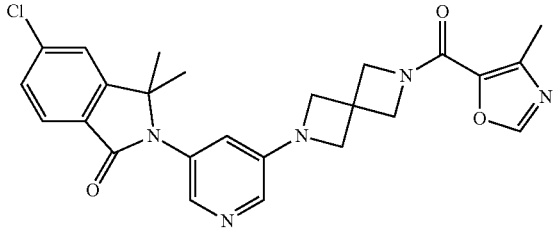<br />White foam | 5-Chloro-2-[5-(2,6-diazaspiro[3.3]heptan-2-yl)-3-pyridyl]-3,3-dimethyl-isoindolin-1-one (intermediate B-3) and 4-methyloxazole-5-carboxylic acid | 478.1 |
| 42 | 5-Chloro-3,3-dimethyl-2-[5-[2-(oxazole-4-carbonyl)-2,6-diazaspiro[3.3]heptan-6-yl]-3-pyridyl]isoindolin-1-one<br />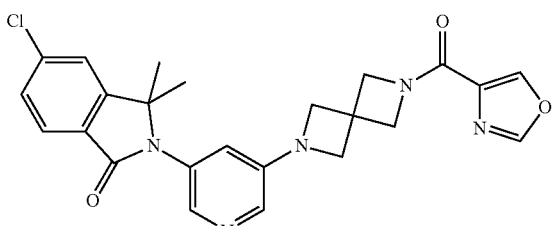<br />White foam | 5-Chloro-2-[5-(2,6-diazaspiro[3.3]heptan-2-yl)-3-pyridyl]-3,3-dimethyl-isoindolin-1-one (intermediate B-3) and oxazole-4-carboxylic acid | 464.1 |
| 43 | 5-Chloro-3,3-dimethyl-2-[5-[2-(2-methyloxazole-5-carbonyl)-2,6-diazaspiro[3.3]heptan-6-yl]-3-pyridyl]isoindolin-1-one<br />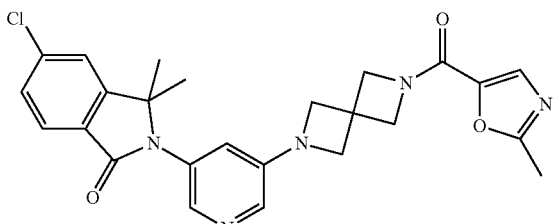<br />White foam | 5-Chloro-2-[5-(2,6-diazaspiro[3.3]heptan-2-yl)-3-pyridyl]-3,3-dimethyl-isoindolin-1-one (intermediate B-3) and 2-methyloxazole-5-carboxylic acid | 478.1 |
| 44 | 5-Chloro-2-[5-[2-(2,4-dimethyloxazole-5-carbonyl)-2,6-diazaspiro[3.3]heptan-6-yl]-3-pyridyl]-3,3-dimethyl-isoindolin-1-one<br />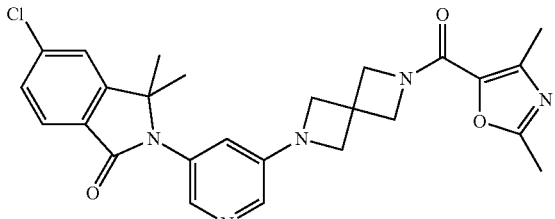<br />White foam | 5-Chloro-2-[5-(2,6-diazaspiro[3.3]heptan-2-yl)-3-pyridyl]-3,3-dimethyl-isoindolin-1-one (intermediate B-3) and 2,4-dimethyloxazole-5-carboxylic acid | 492.1 |

TABLE 1-continued

| Example | Name Structure Aspect | Reactants | MS (M + H+) |
|---|---|---|---|
| 45 | 5-Chloro-3,3-dimethyl-2-[5-[2-(2-methyloxazole-4-carbonyl)-2,6-diazaspiro[3.3]heptan-6-yl]-3-pyridyl]isoindolin-1-one<br>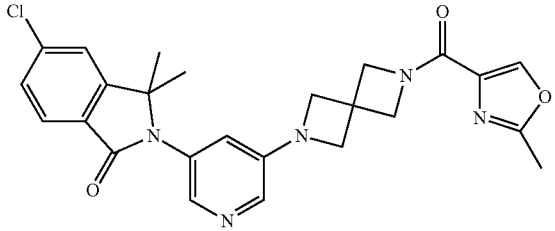<br>White foam | 5-Chloro-2-[5-(2,6-diazaspiro[3.3]heptan-2-yl)-3-pyridyl]-3,3-dimethyl-isoindolin-1-one (intermediate B-3) and 2-methyloxazole-4-carboxylicacid | 478.1 |
| 46 | 2-[6-[5-(6-Chloro-1,1-dimethyl-3-oxo-isoindolin-2-yl)-3-pyridyl]-2,6-diazaspiro[3.3]heptan-2-carbonyl]pyridine-3-carbonitrile<br>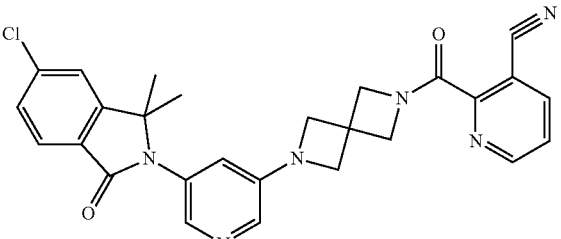<br>White foam | 5-Chloro-2-[5-(2,6-diazaspiro[3.3]heptan-2-yl)-3-pyridyl]-3,3-dimethyl-isoindolin-1-one (intermediate B-3) and 3-cyanopyridine-2-carboxylic acid | 499.1 |
| 47 | 5-Chloro-2-[5-[2-(5-chloro-2-methyl-pyrimidine-4-carbonyl)-2,6-diazaspiro[3.3]heptan-6-yl]-3-pyridyl]-3,3-dimethyl-isoindolin-1-one<br>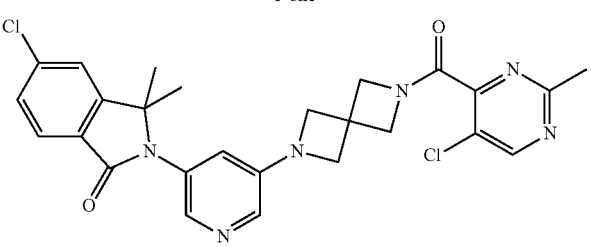<br>White foam | 5-Chloro-2-[5-(2,6-diazaspiro[3.3]heptan-2-yl)-3-pyridyl]-3,3-dimethyl-isoindolin-1-one (intermediate B-3) and 5-chloro-2-methyl-pyrimidine-4-carboxylic acid | 523.1 |
| 48 | 5-Chloro-2-[5-[2-(4,6-dimethylpyrimidine-5-carbonyl)-2,6-diazaspiro[3.3]heptan-6-yl]-3-pyridyl]-3,3-dimethyl-isoindolin-1-one<br>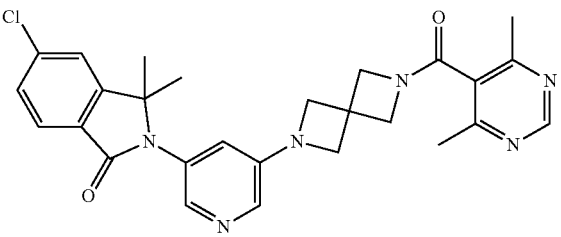<br>White foam | 5-Chloro-2-[5-(2,6-diazaspiro[3.3]heptan-2-yl)-3-pyridyl]-3,3-dimethyl-isoindolin-1-one (intermediate B-3) and 4,6-dimethylpyrimidine-5-carboxylic acid | 503.1 |

TABLE 1-continued

| Example | Name Structure Aspect | Reactants | MS (M + H+) |
|---|---|---|---|
| 49 | 5-Chloro-2-[5-[2-(2,4-dimethylpyridine-3-carbonyl)-2,6-diazaspiro[3.3]heptan-6-yl]-3-pyridyl]-3,3-dimethyl-isoindolin-1-one<br />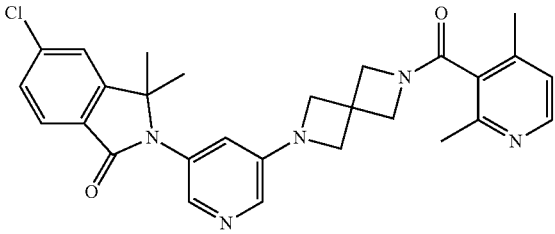<br />White foam | 5-Chloro-2-[5-(2,6-diazaspiro[3.3]heptan-2-yl)-3-pyridyl]-3,3-dimethyl-isoindolin-1-one (intermediate B-3) and 2,4-dimethylpyridine-3-carboxylic acid | 502.1 |
| 50 | 3-[6-[5-(6-Chloro-1,1-dimethyl-3-oxo-isoindolin-2-yl)-3-pyridyl]-2,6-diazaspiro[3.3]heptane-2-carbonyl]pyridine-4-carbonitrile<br />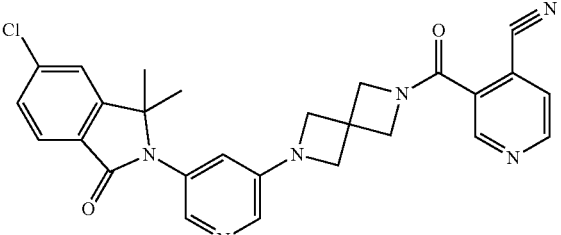<br />White foam | 5-Chloro-2-[5-(2,6-diazaspiro[3.3]heptan-2-yl)-3-pyridyl]-3,3-dimethyl-isoindolin-1-one (intermediate B-3) and 4-cyanopyridine-3-carboxylic acid | 499.1 |
| 51 | (3S or 3R)-5-Chloro-2-[5-[2-(1-ethylpyrazole-4-carbonyl)-2,6-diazaspiro[3.3]heptan-6-yl]-3-pyridyl]-3-methyl-isoindolin-1-one<br />Chiral<br />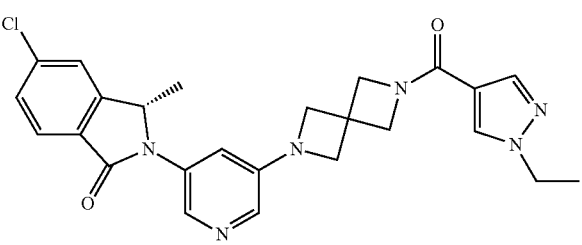<br />White foam | 5-Chloro-2-[5-(2,6-diazaspiro[3.3]heptan-2-yl)-3-pyridyl]-3-methyl-isoindolin-1-one (intermediate B-2) and 1-ethylpyrazole-4-carboxylic acid<br />Chiral separation | 477.2 |

TABLE 1-continued

| Example | Name Structure Aspect | Reactants | MS (M + H+) |
|---|---|---|---|
| 52 | (3R or 3S)-5-Chloro-2-[5-[2-(1-ethylpyrazole-4-carbonyl)-2,6-diazaspiro[3.3]heptan-6-yl]-3-pyridyl]-3-methyl-isoindolin-1-one<br>Chiral<br>White foam | 5-Chloro-2-[5-(2,6-diazaspiro[3.3]heptan-2-yl)-3-pyridyl]-3-methyl-isoindolin-1-one (intermediate B-2) and 1-ethylpyrazole-4-carboxylic acid<br>Chiral separation | 477.2 |
| 53 | 6-Chloro-2-[5-[2-(1-methylpyrazole-4-carbonyl)-2,6-diazaspiro[3.3]heptan-6-yl]-3-pyridyl]-3,4-dihydroisoquinolin-1-one<br>White foam | 6-Chloro-2-[5-(2,6-diazaspiro[3.3]heptan-2-yl)-3-pyridyl]-3,4-dihydroisoquinolin-1-one (intermediate B-1) and 1-methylpyrazole-4-carboxylic acid | 463.1 |
| 54 | (3R or 3S)-5-Chloro-3-methyl-2-[4-methyl-5-[2-(1-methylpyrazole-4-carbonyl)-2,6-diazaspiro[3.3]heptan-6-yl]-3-pyridyl]isoindolin-1-one<br>Chiral<br>White foam | 5-Chloro-2-[5-(2,6-diazaspiro[3.3]heptan-2-yl)-4-methyl-3-pyridyl]-3-methyl-isoindolin-1-one (intermediate B-7) and 1-methylpyrazole-4-carboxylic acid<br>Chiral separation | 477.1 |

TABLE 1-continued

| Example | Name Structure Aspect | Reactants | MS (M + H+) |
|---|---|---|---|
| 55 | (3S or 3R)-5-Chloro-3-methyl-2-[4-methyl-5 or 3-[2-(1-methylpyrazole-4-carbonyl)-2,6-diazaspiro[3.3]heptan-6-yl]-3-pyridyl]isoindolin-1-one<br>Chiral<br>White foam | 5-Chloro-2-[5-(2,6-diazaspiro[3.3]heptan-2-yl)-4-methyl-3-pyridyl]-methyl-isoindolin-1-one (intermediate B-7) and 1 methylpyrazole-4-carboxylic acid<br>Chiral separation | 477.3 |
| 56 | 5-Chloro-3,3-dimethyl-2-[5-[7-(1-methylpyrazole-4-carbonyl)-2,7-diazaspiro[3.5]nonan-2-yl]-3-pyridyl]isoindolin-1-one<br>White foam | 5-Chloro-2-[5-(2,7-diazaspiro[3.5]nonan-2-yl)-3-pyridyl]-3,3-dimethyl-isoindolin-1-one (intermediate B-8) and 1-methylpyrazole-4-carboxylic acid | 505.1 |
| 57 | 5-Chloro-3,3-dimethyl-2-[5-[7-(4-methylpyridine-3-carbonyl)-2,7-diazaspiro[3.5]nonan-2-yl]-3-pyridyl]isoindolin-1-one<br>White foam | 5-Chloro-2-[5-(2,7-diazaspiro[3.5]nonan-2-yl)-3-pyridyl]-3,3-dimethyl-isoindolin-1-one (intermediate B-8) and 4-methylpyridine-3-carboxylic acid | 516.1 |

TABLE 1-continued

| Example | Name Structure Aspect | Reactants | MS (M + H+) |
|---|---|---|---|
| 58 | 5-Chloro-2-[5-[7-(1-ethylpyrazole-4-carbonyl)-2,7-diazaspiro[3.5]nonan-2-yl]-3-pyridyl]-3,3-dimethyl-isoindolin-1-one<br />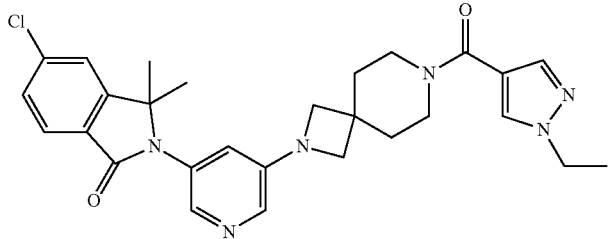<br />White foam | 5-Chloro-2-[5-(2,7-diazaspiro[3.5]nonan-2-yl)-3-pyridyl]-3,3-dimethyl-isoindolin-1-one (intermediate B-8) and 1-ethylpyrazole-4-carboxylic acid | 519.1 |
| 59 | 5-Chloro-3,3-dimethyl-2-[5-[2-(1-methylpyrazole-4-carbonyl)-2,7-diazaspiro[3.5]nonan-7-yl]-3-pyridyl]isoindolin-1-one<br />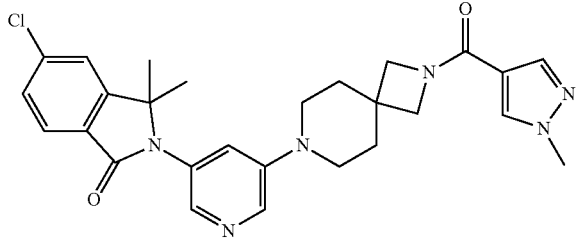<br />White foam | 5-Chloro-2-[5-(2,7-diazaspiro[3.5]nonan-7-yl)-3-pyridyl]-3,3-dimethyl-isoindolin-1-one (intermediate B-9) and 1-methylpyrazole-4-carboxylic acid | 505.1 |
| 60 | 5-Chloro-2-[5-[2-(1-ethylpyrazole-4-carbonyl)-2,7-diazaspiro[3.5]nonan-7-yl]-3-pyridyl]-3,3-dimethyl-isoindolin-1-one<br />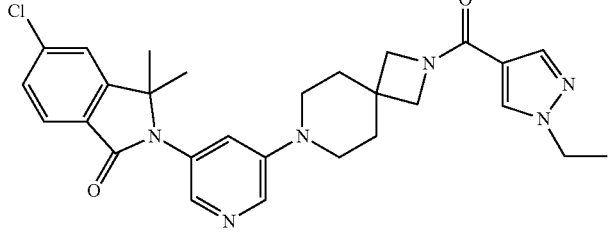<br />White foam | 5-Chloro-2-[5-(2,7-diazaspiro[3.5]nonan-7-yl)-3-pyridyl]-3,3-dimethyl-isoindolin-1-one (intermediate B-9) and 1-ethylpyrazole-4-carboxylic acid | 519.1 |

TABLE 1-continued

| Example | Name<br>Structure<br>Aspect | Reactants | MS<br>(M + H+) |
|---|---|---|---|
| 61 | 5-Chloro-3,3-dimethyl-2-[5-[2-(4-methylpyridine-3-carbonyl)-2,7-diazaspiro[3.5]nonan-7-yl]-3-pyridyl]isoindolin-1-one<br><br>White foam | 5-Chloro-2-[5-(2,7-diazaspiro[3.5]nonan-7-yl)-3-pyridyl]-3,3-dimethyl-isoindolin-1-one (intermediate B-9) and 4-methylpyridine-3-carboxylic acid | 516.1 |

Example A

A compound of formula (I) can be used in a manner known per se as the active ingredient for the production of tablets of the following composition:

Per Tablet

| | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

Per Capsule

| | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

We claim:
1. Compounds of formula (I)

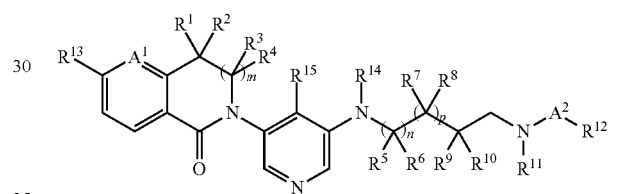

wherein
$R^1$, $R^2$, $R^3$ and $R^4$ are independently selected from H, alkyl and cycloalkyl;
or $R^1$ and $R^2$ together form —$CH_2$—$CH_2$—;
$R^5$ and $R^6$ are independently selected from H or alkyl;
$A^1$ is —CH— or —N—;
$A^2$ is —C(O)— or —S(O)$_2$—;
$R^{12}$ is heteroaryl or substituted heteroaryl, wherein substituted heteroaryl is substituted with one to three substituent independently selected from alkyl, cycloalkyl, haloalkyl, hydroxy, alkoxy, cyano and halogen;
$R^{13}$ is halogen, cyano, alkoxy or haloalkoxy;
$R^{15}$ is H, alkyl, cycloalkyl or halogen;
m is zero or 1; and
$R^{14}$ and (i) $R^9$ together are —$CH_2$—, $R^{10}$ and $R^{11}$ together are —$CH_2$—, n is 1 and p is zero; or (ii) $R^9$ together are —$CH_2$—$CH_2$—, $R^{10}$ and $R^{11}$ together are —$CH_2$—, n is 1 and p is 1 and $R^7$ and $R^8$ are independently selected from H or alkyl; or (iii) $R^7$ together are —$CH_2$—, $R^8$ and $R^{11}$ together are —$CH_2$—$CH_2$—, n is 1, p is 1 and $R^9$ and $R^{10}$ are independently selected from H or alkyl;
or, a pharmaceutically acceptable salt thereof.

2. The compound according to claim 1, wherein $R^1$ and $R^2$ are alkyl or $R^1$ and $R^2$ together form —$CH_2$—$CH_2$—.

3. The compound according to claim 1 wherein $R^1$ and $R^2$ are alkyl.

4. The compound according to claim 1 wherein $R^3$ and $R^4$ are H.

5. The compound according to claim 1 wherein $R^{13}$ is halogen.

6. The compound according to claim 1 wherein $R^{15}$ is H.

7. The compound according to claim 1 wherein $A^1$ is —CH—.

8. The compound according to claim 1 wherein $A^2$ is —C(O)—.

9. The compound according to claim 1 wherein $R^9$ and $R^{14}$ together form —CH$_2$—, $R^{10}$ and $R^{11}$ together form —CH$_2$—, n is 1 and p is zero.

10. The compound according to claim 1 wherein $R^{12}$ is a heteroaryl group selected from the group consisting of imidazolyl, isoxazolyl, oxazolyl, pyrazinyl, pyrazolyl, pyridazinyl, pyridinyl and pyrimidinyl.

11. The compound of claim 1 wherein $A^1$ is —CH$_2$— and $A^2$ is —C(O)—.

12. The compound of claim 11 wherein $R^{12}$ is a heteroaryl group selected from the group consisting of imidazolyl, isoxazolyl, oxazolyl, pyrazinyl, pyrazolyl, pyridazinyl, pyridinyl and pyrimidinyl.

13. The compound according to claim 1 wherein $R^{12}$ is pyrazolyl substituted by alkyl or is pyridinyl substituted by alkyl.

14. The compound according to claim 11, wherein $R^{12}$ is pyrazolyl substituted by alkyl.

15. The compound according to claim 1 which compound is selected from the group consisting of:
   5-Chloro-3,3-dimethyl-2-[5-[2-(1-methylpyrazole-4-carbonyl)-2,6-diazaspiro[3.3]heptan-6-yl]-3-pyridyl]isoindolin-1-one;
   5-Chloro-2-[5-[2-(1-ethylpyrazole-4-carbonyl)-2,6-diazaspiro[3.3]heptan-6-yl]-3-pyridyl]-3,3-dimethyl-isoindolin-1-one;
   5-Chloro-2-[5-[2-(1-isopropylpyrazole-4-carbonyl)-2,6-diazaspiro[3.3]heptan-6-yl]-3-pyridyl]-3,3-dimethyl-isoindolin-1-one;
   5-Chloro-3,3-dimethyl-2-[5-[2-(1-methylimidazole-2-carbonyl)-2,6-diazaspiro[3.3]heptan-6-yl]-3-pyridyl]isoindolin-1-one;
   5-Chloro-3,3-dimethyl-2-[5-[2-(2-methylpyrazole-3-carbonyl)-2,6-diazaspiro[3.3]heptan-6-yl]-3-pyridyl]isoindolin-1-one;
   5-Chloro-3,3-dimethyl-2-[5-[2-(3-methylimidazole-4-carbonyl)-2,6-diazaspiro[3.3]heptan-6-yl]-3-pyridyl]isoindolin-1-one;
   5-Chloro-3,3-dimethyl-2-[5-[2-(4-methylpyridine-3-carbonyl)-2,6-diazaspiro[3.3]heptan-6-yl]-3-pyridyl]isoindolin-1-one;
   3,3-Dimethyl-2-[5-[2-(1-methylpyrazole-4-carbonyl)-2,6-diazaspiro[3.3]heptan-6-yl]-3-pyridyl]-1-oxo-isoindoline-5-carbonitrile;
   2-[5-[2-(1-Ethylpyrazole-4-carbonyl)-2,6-diazaspiro[3.3]heptan-6-yl]-3-pyridyl]-3,3-dimethyl-1-oxo-isoindoline-5-carbonitrile;
   2-[5-[2-(1-Isopropylpyrazole-4-carbonyl)-2,6-diazaspiro[3.3]heptan-6-yl]-3-pyridyl]-3,3-dimethyl-1-oxo-isoindoline-5-carbonitrile;
   3,3-Dimethyl-2-[5-[2-(1-methylimidazole-2-carbonyl)-2,6-diazaspiro[3.3]heptan-6-yl]-3-pyridyl]-1-oxo-isoindoline-5-carbonitrile;
   3,3-Dimethyl-2-[5-[2-(2-methylpyrazole-3-carbonyl)-2,6-diazaspiro[3.3]heptan-6-yl]-3-pyridyl]-1-oxo-isoindoline-5-carbonitrile;
   3,3-Dimethyl-2-[5-[2-(3-methylimidazole-4-carbonyl)-2,6-diazaspiro[3.3]heptan-6-yl]-3-pyridyl]-1-oxo-isoindoline-5-carbonitrile;
   3,3-Dimethyl-2-[5-[2-(4-methylpyridine-3-carbonyl)-2,6-diazaspiro[3.3]heptan-6-yl]-3-pyridyl]-1-oxo-isoindoline-5-carbonitrile;
   2-Methoxy-7,7-dimethyl-6-[5-[2-(1-methylpyrazole-4-carbonyl)-2,6-diazaspiro[3.3]heptan-6-yl]-3-pyridyl]pyrrolo[3,4-b]pyridin-5-one;
   2-Methoxy-7,7-dimethyl-6-[5-[2-(4-methylpyridine-3-carbonyl)-2,6-diazaspiro[3.3]heptan-6-yl]-3-pyridyl]pyrrolo[3,4-b]pyridin-5-one;
   2-Methoxy-7,7-dimethyl-6-[5-[2-(2-methylpyrazole-3-carbonyl)-2,6-diazaspiro[3.3]heptan-6-yl]-3-pyridyl]pyrrolo[3,4-b]pyridin-5-one;
   5-Chloro-3-methyl-2-[5-[2-(1-methylpyrazole-4-carbonyl)-2,6-diazaspiro[3.3]heptan-6-yl]-3-pyridyl]isoindolin-1-one;
   5'-Chloro-2'-[5-[2-(1-methylpyrazole-4-carbonyl)-2,6-diazaspiro[3.3]heptan-6-yl]-3-pyridyl]spiro[cyclopropane-1,3'-isoindoline]-1'-one;
   5'-Chloro-2'-[5-[2-(4-methylpyridine-3-carbonyl)-2,6-diazaspiro[3.3]heptan-6-yl]-3-pyridyl]spiro[cyclopropane-1,3'-isoindoline]-1'-one;
   5'-Chloro-2'-[5-[2-(2-methylpyrazole-3-carbonyl)-2,6-diazaspiro[3.3]heptan-6-yl]-3-pyridyl]spiro[cyclopropane-1,3'-isoindoline]-1'-one;
   (3R or 3S)-5-Chloro-3-methyl-2-[5-[2-(1-methylpyrazole-4-carbonyl)-2,6-diazaspiro[3.3]heptan-6-yl]-3-pyridyl]isoindolin-1-one;
   (3S or 3R)-5-Chloro-3-methyl-2-[5-[2-(1-methylpyrazole-4-carbonyl)-2,6-diazaspiro[3.3]heptan-6-yl]-3-pyridyl]isoindolin-1-one;
   5-Chloro-2-[5-[2-(4-methoxypyridine-3-carbonyl)-2,6-diazaspiro[3.3]heptan-6-yl]-3-pyridyl]-3,3-dimethyl-isoindolin-1-one;
   5-Chloro-2-[5-[2-(3,6-dimethylpyrazine-2-carbonyl)-2,6-diazaspiro[3.3]heptan-6-yl]-3-pyridyl]-3,3-dimethyl-isoindolin-1-one;
   5-Chloro-2-[5-[2-(1,5-dimethylpyrazole-4-carbonyl)-2,6-diazaspiro[3.3]heptan-6-yl]-3-pyridyl]-3,3-dimethyl-isoindolin-1-one;
   5-Chloro-3,3-dimethyl-2-[5-[2-(3-methylisoxazole-4-carbonyl)-2,6-diazaspiro[3.3]heptan-6-yl]-3-pyridyl]isoindolin-1-one;
   5-Chloro-3,3-dimethyl-2-[5-[2-(6-methylpyrazine-2-carbonyl)-2,6-diazaspiro[3.3]heptan-6-yl]-3-pyridyl]isoindolin-1-one;
   5-Chloro-3,3-dimethyl-2-[5-[2-(4-methylpyrimidine-5-carbonyl)-2,6-diazaspiro[3.3]heptan-6-yl]-3-pyridyl]isoindolin-1-one;
   5-Chloro-3,3-dimethyl-2-[5-[2-(5-methylpyrazine-2-carbonyl)-2,6-diazaspiro[3.3]heptan-6-yl]-3-pyridyl]isoindolin-1-one;
   5-Chloro-2-[5-[2-(2,5-dimethylpyrazole-3-carbonyl)-2,6-diazaspiro[3.3]heptan-6-yl]-3-pyridyl]-3,3-dimethyl-isoindolin-1-one;
   5-Chloro-3,3-dimethyl-2-[5-[2-(5-methyloxazole-4-carbonyl)-2,6-diazaspiro[3.3]heptan-6-yl]-3-pyridyl]isoindolin-1-one;
   5-Chloro-3,3-dimethyl-2-[5-[2-(pyrimidine-2-carbonyl)-2,6-diazaspiro[3.3]heptan-6-yl]-3-pyridyl]isoindolin-1-one;
   5-Chloro-3,3-dimethyl-2-[5-[2-(5-methylpyrimidine-2-carbonyl)-2,6-diazaspiro[3.3]heptan-6-yl]-3-pyridyl]isoindolin-1-one;
   5-Chloro-2-[5-[2-[3-(difluoromethyl)-1-methyl-pyrazole-4-carbonyl]-2,6-diazaspiro[3.3]heptan-6-yl]-3-pyridyl]-3,3-dimethyl-isoindolin-1-one;
   5-[6-[5-(6-Chloro-1,1-dimethyl-3-oxo-isoindolin-2-yl)-3-pyridyl]-2,6-diazaspiro[3.3]heptane-2-carbonyl]pyridine-3-carbonitrile;

5-Chloro-2-[5-[2-(3-methoxypyrazine-2-carbonyl)-2,6-diazaspiro[3.3]heptan-6-yl]-3-pyridyl]-3,3-dimethyl-isoindolin-1-one;

5-Chloro-3,3-dimethyl-2-[5-[2-(pyrazine-2-carbonyl)-2,6-diazaspiro[3.3]heptan-6-yl]-3-pyridyl]isoindolin-1-one;

5-Chloro-3,3-dimethyl-2-[5-[2-(5-methylisoxazole-4-carbonyl)-2,6-diazaspiro[3.3]heptan-6-yl]-3-pyridyl]isoindolin-1-one;

5-Chloro-3,3-dimethyl-2-[5-[2-(pyrimidine-5-carbonyl)-2,6-diazaspiro[3.3]heptan-6-yl]-3-pyridyl]isoindolin-1-one;

5-Chloro-3,3-dimethyl-2-[5-[2-(4-methyloxazole-5-carbonyl)-2,6-diazaspiro[3.3]heptan-6-yl]-3-pyridyl]isoindolin-1-one;

5-Chloro-3,3-dimethyl-2-[5-[2-(oxazole-4-carbonyl)-2,6-diazaspiro[3.3]heptan-6-yl]-3-pyridyl]isoindolin-1-one;

5-Chloro-3,3-dimethyl-2-[5-[2-(2-methyloxazole-5-carbonyl)-2,6-diazaspiro[3.3]heptan-6-yl]-3-pyridyl]isoindolin-1-one;

5-Chloro-2-[5-[2-(2,4-dimethyloxazole-5-carbonyl)-2,6-diazaspiro[3.3]heptan-6-yl]-3-pyridyl]-3,3-dimethyl-isoindolin-1-one;

5-Chloro-3,3-dimethyl-2-[5-[2-(2-methyloxazole-4-carbonyl)-2,6-diazaspiro[3.3]heptan-6-yl]-3-pyridyl]isoindolin-1-one;

2-[6-[5-(6-Chloro-1,1-dimethyl-3-oxo-isoindolin-2-yl)-3-pyridyl]-2,6-diazaspiro[3.3]heptane-2-carbonyl]pyridine-3-carbonitrile;

5-Chloro-2-[5-[2-(5-chloro-2-methyl-pyrimidine-4-carbonyl)-2,6-diazaspiro[3.3]heptan-6-yl]-3-pyridyl]-3,3-dimethyl-isoindolin-1-one;

5-Chloro-2-[5-[2-(4,6-dimethylpyrimidine-5-carbonyl)-2,6-diazaspiro[3.3]heptan-6-yl]-3-pyridyl]-3,3-dimethyl-isoindolin-1-one;

5-Chloro-2-[5-[2-(2,4-dimethylpyridine-3-carbonyl)-2,6-diazaspiro[3.3]heptan-6-yl]-3-pyridyl]-3,3-dimethyl-isoindolin-1-one;

3-[6-[5-(6-Chloro-1,1-dimethyl-3-oxo-isoindolin-2-yl)-3-pyridyl]-2,6-diazaspiro[3.3]heptane-2-carbonyl]pyridine-4-carbonitrile;

(3S or 3R)-5-Chloro-2-[5-[2-(1-ethylpyrazole-4-carbonyl)-2,6-diazaspiro[3.3]heptan-6-yl]-3-pyridyl]-3-methyl-isoindolin-1-one;

(3R or 3S)-5-Chloro-2-[5-[2-(1-ethylpyrazole-4-carbonyl)-2,6-diazaspiro[3.3]heptan-6-yl]-3-pyridyl]-3-methyl-isoindolin-1-one;

6-Chloro-2-[5-[2-(1-methylpyrazole-4-carbonyl)-2,6-diazaspiro[3.3]heptan-6-yl]-3-pyridyl]-3,4-dihydroisoquinolin-1-one;

(3R or 3S)-5-Chloro-3-methyl-2-[4-methyl-5-[2-(1-methylpyrazole-4-carbonyl)-2,6-diazaspiro[3.3]heptan-6-yl]-3-pyridyl]isoindolin-1-one;

(3S or 3R)-5-Chloro-3-methyl-2-[4-methyl-5-[2-(1-methylpyrazole-4-carbonyl)-2,6-diazaspiro[3.3]heptan-6-yl]-3-pyridyl]isoindolin-1-one;

5-Chloro-3,3-dimethyl-2-[5-[7-(1-methylpyrazole-4-carbonyl)-2,7-diazaspiro[3.5]nonan-2-yl]-3-pyridyl]isoindolin-1-one;

5-Chloro-3,3-dimethyl-2-[5-[7-(4-methylpyridine-3-carbonyl)-2,7-diazaspiro[3.5]nonan-2-yl]-3-pyridyl]isoindolin-1-one;

5-Chloro-2-[5-[7-(1-ethylpyrazole-4-carbonyl)-2,7-diazaspiro[3.5]nonan-2-yl]-3-pyridyl]-3,3-dimethyl-isoindolin-1-one;

5-Chloro-3,3-dimethyl-2-[5-[2-(1-methylpyrazole-4-carbonyl)-2,7-diazaspiro[3.5]nonan-7-yl]-3-pyridyl]isoindolin-1-one;

5-Chloro-2-[5-[2-(1-ethylpyrazole-4-carbonyl)-2,7-diazaspiro[3.5]nonan-7-yl]-3-pyridyl]-3,3-dimethyl-isoindolin-1-one; and, 5-Chloro-3,3-dimethyl-2-[5-[2-(4-methylpyridine-3-carbonyl)-2,7-diazaspiro[3.5]nonan-7-yl]-3-pyridyl]isoindolin-1-one; or, a pharmaceutically acceptable salt thereof.

16. The compound according to claim 1 which compound is selected from the group consisting of:

5-Chloro-3,3-dimethyl-2-[5-[2-(1-methylpyrazole-4-carbonyl)-2,6-diazaspiro[3.3]heptan-6-yl]-3-pyridyl]isoindolin-1-one;

5-Chloro-2-[5-[2-(1-ethylpyrazole-4-carbonyl)-2,6-diazaspiro[3.3]heptan-6-yl]-3-pyridyl]-3,3-dimethyl-isoindolin-1-one;

5-Chloro-3,3-dimethyl-2-[5-[2-(4-methylpyridine-3-carbonyl)-2,6-diazaspiro[3.3]heptan-6-yl]-3-pyridyl]isoindolin-1-one;

2-[5-[2-(1-Ethylpyrazole-4-carbonyl)-2,6-diazaspiro[3.3]heptan-6-yl]-3-pyridyl]-3,3-dimethyl-1-oxo-isoindoline-5-carbonitrile;

2-Methoxy-7,7-dimethyl-6-[5-[2-(1-methylpyrazole-4-carbonyl)-2,6-diazaspiro[3.3]heptan-6-yl]-3-pyridyl]pyrrolo[3,4-b]pyridin-5-one;

5'-Chloro-2'-[5-[2-(1-methylpyrazole-4-carbonyl)-2,6-diazaspiro[3.3]heptan-6-yl]-3-pyridyl]spiro[cyclopropane-1,3'-isoindoline]-1'-one;

5-Chloro-3,3-dimethyl-2-[5-[7-(1-methylpyrazole-4-carbonyl)-2,7-diazaspiro[3.5]nonan-2-yl]-3-pyridyl]isoindolin-1-one;

5-Chloro-2-[5-[7-(1-ethylpyrazole-4-carbonyl)-2,7-diazaspiro[3.5]nonan-2-yl]-3-pyridyl]-3,3-dimethyl-isoindolin-1-one; and, 5-Chloro-3,3-dimethyl-2-[5-[2-(1-methylpyrazole-4-carbonyl)-2,7-diazaspiro[3.5]nonan-7-yl]-3-pyridyl]isoindolin-1-one; or, or a pharmaceutically acceptable salt thereof.

17. A process to prepare a compound according to claim 1 comprising reacting a compound of formula (II) with a compound of formula (III) to afford compound I wherein $R^1$, $R^2$, $R^3$,

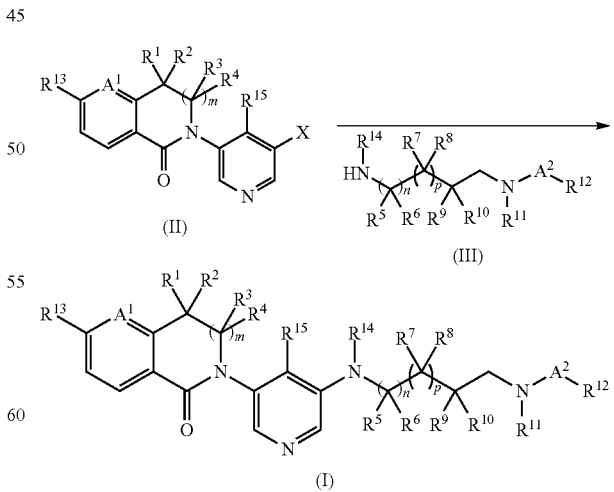

$R^4$, $R^5$, $R^6$, $R^7$, $R^8$, $R^9$, $R^{10}$, $R^{11}$, $R^{12}$, $R^{13}$, $R^{14}$, $A^1$, $A^2$ m, n and p are as described in claim 1 and X is halogen or triflate.

18. A process to prepare a compound according to claim 1 comprising reacting a compound of formula (IV) with a compound of formula (V) to afford a compound of formula (I)

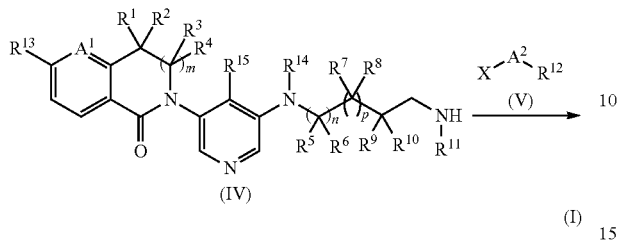

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $A^1$, $A^2$ m, n and p are as described in claim 1 and X is halogen.

19. A pharmaceutical composition comprising a compound according to claim 1 and at least one therapeutically acceptable carrier, diluent or excipient.

20. A method for the treatment of chronic kidney disease, congestive heart failure, hypertension, primary aldosteronism and Cushing syndrome, which method comprises administering to a patient in need thereof, a therapeutically effective amount of a compound according to claim 1.

* * * * *